United States Patent
Mooney et al.

(10) Patent No.: US 11,944,581 B2
(45) Date of Patent: *Apr. 2, 2024

(54) SYSTEMS AND METHODS FOR BILATERAL WIRELESS COMMUNICATION

(71) Applicant: Dephy, Inc., Maynard, MA (US)

(72) Inventors: Luke Mooney, Sudbury, MA (US); Jean-François Duval, Belmont, MA (US); Rachel Harris, Cambridge, MA (US)

(73) Assignee: Dephy, Inc., Maynard, MA (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/504,248

(22) Filed: Oct. 18, 2021

(65) Prior Publication Data

US 2022/0031552 A1 Feb. 3, 2022

Related U.S. Application Data

(63) Continuation of application No. 17/084,111, filed on Oct. 29, 2020, now Pat. No. 11,147,733.

(Continued)

(51) Int. Cl.
*A61H 3/00* (2006.01)
*G16H 20/30* (2018.01)
*G16H 40/67* (2018.01)

(52) U.S. Cl.
CPC ............... *A61H 3/00* (2013.01); *G16H 20/30* (2018.01); *G16H 40/67* (2018.01);
(Continued)

(58) Field of Classification Search
CPC ................ A61H 3/00; A61H 2003/007; A61H 2201/1207; A61H 2201/1642;
(Continued)

(56) References Cited

U.S. PATENT DOCUMENTS 2,477,591 A  8/1949 Follis
2,516,872 A  8/1950 Hauser et al.
(Continued)

FOREIGN PATENT DOCUMENTS

CA  2937610 A1  7/2009
CN  202679044 U  1/2013
(Continued)

OTHER PUBLICATIONS

International Preliminary Report on Patentability on PCT Appl. Ser. No. PCT/US2020/059866 dated May 27, 2022 (14 pages).

(Continued)

*Primary Examiner* — Timothy A Stanis
(74) *Attorney, Agent, or Firm* — Foley & Lardner LLP

(57) ABSTRACT

Systems and methods for communicating between multiple lower limb exoskeletons are provided. A first exoskeleton boot can receive, responsive to transmitting a first packet, a second packet from a second exoskeleton boot through a wireless connection between the first exoskeleton boot and the second exoskeleton boot. The first exoskeleton boot can determine a latency for communication between the first exoskeleton boot and the second exoskeleton boot based on a time difference between transmission of the first packet and receipt of the second packet and update, responsive to the comparison, a model indicating data weighted based on the latency for controlling the first exoskeleton boot and the second exoskeleton boot. The first exoskeleton boot can generate, using data from the model, a command to cause an electric motor of the first exoskeleton boot to generate torque to aid a limb of a user in performing a movement.

20 Claims, 16 Drawing Sheets

Related U.S. Application Data

(60) Provisional application No. 63/034,748, filed on Jun. 4, 2020.

(52) U.S. Cl.
CPC .......... *A61H 2003/007* (2013.01); *A61H 2201/1207* (2013.01); *A61H 2201/1642* (2013.01); *A61H 2201/165* (2013.01); *A61H 2201/5097* (2013.01)

(58) Field of Classification Search
CPC ..... A61H 2201/165; A61H 2201/5097; G16H 20/30; G16H 40/67
See application file for complete search history.

(56) References Cited

U.S. PATENT DOCUMENTS

| | | | |
|---|---|---|---|
| 2,573,698 A | 11/1951 | Ellery | |
| 3,064,644 A | 11/1962 | Patterson | |
| 5,490,831 A | 2/1996 | Myers et al. | |
| 5,685,830 A | 11/1997 | Bonutti | |
| 6,299,588 B1 | 10/2001 | Fratrick | |
| 6,872,187 B1 | 3/2005 | Stark et al. | |
| 7,153,242 B2 | 12/2006 | Goffer | |
| 7,431,737 B2 | 10/2008 | Ragnarsdottir et al. | |
| 7,531,006 B2 | 5/2009 | Clausen et al. | |
| 7,628,766 B1 | 12/2009 | Kazerooni et al. | |
| 7,811,333 B2 | 10/2010 | Jonsson et al. | |
| 8,114,168 B2 | 2/2012 | Olafsson et al. | |
| 8,435,309 B2 | 5/2013 | Gilbert et al. | |
| 8,516,918 B2 | 8/2013 | Jacobsen et al. | |
| 8,585,620 B2 | 11/2013 | McBean et al. | |
| 8,597,369 B2 | 12/2013 | Hansen et al. | |
| 8,734,528 B2 | 5/2014 | Herr et al. | |
| 8,764,850 B2 | 7/2014 | Hansen et al. | |
| 8,784,350 B2 | 7/2014 | Cohen | |
| 8,790,282 B2 | 7/2014 | Jung et al. | |
| 8,801,802 B2 | 8/2014 | Oddsson et al. | |
| 8,864,846 B2 | 10/2014 | Herr et al. | |
| 8,870,801 B2 | 10/2014 | Tomiyama et al. | |
| 8,870,967 B2 | 10/2014 | Herr et al. | |
| 9,017,419 B1 | 4/2015 | Landry et al. | |
| 9,066,819 B2 | 6/2015 | Gramnaes | |
| 9,078,774 B2 | 7/2015 | Jonsson et al. | |
| 9,198,821 B2 | 12/2015 | Unluhisarcikli et al. | |
| 9,333,097 B2 | 5/2016 | Herr et al. | |
| 9,339,397 B2 | 5/2016 | Herr et al. | |
| 9,345,608 B2 | 5/2016 | Phillips | |
| 9,480,618 B2 | 11/2016 | Hsiao-Wecksler et al. | |
| 9,539,117 B2 | 1/2017 | Herr et al. | |
| 9,554,922 B2 | 1/2017 | Casler et al. | |
| 9,662,262 B2 | 5/2017 | Hollander et al. | |
| 9,693,883 B2 | 7/2017 | Herr et al. | |
| 9,707,104 B2 | 7/2017 | Clausen | |
| 9,737,419 B2 | 8/2017 | Herr et al. | |
| 9,808,390 B2 | 11/2017 | Caires et al. | |
| 9,839,552 B2 | 12/2017 | Han et al. | |
| 9,872,782 B2 | 1/2018 | Herr et al. | |
| 9,907,722 B2 | 3/2018 | Aguirre-Ollinger et al. | |
| 9,925,071 B2 | 3/2018 | Langlois et al. | |
| 9,980,873 B2 | 5/2018 | Tung et al. | |
| 10,195,057 B2 | 2/2019 | Clausen | |
| 10,251,762 B2 | 4/2019 | Langlois | |
| 10,307,271 B2 | 6/2019 | Holgate et al. | |
| 10,307,272 B2 | 6/2019 | Herr et al. | |
| 10,335,294 B2 | 7/2019 | Huang et al. | |
| 10,369,023 B2 | 8/2019 | Simon et al. | |
| 10,405,996 B2 | 9/2019 | Langlois | |
| 10,406,002 B2 | 9/2019 | Herr et al. | |
| 10,426,637 B2 | 10/2019 | Tong et al. | |
| 10,463,561 B2 | 11/2019 | Zhang et al. | |
| 10,485,681 B2 | 11/2019 | Herr et al. | |
| 10,532,000 B1 | 1/2020 | De Sapio et al. | |
| 10,537,449 B2 | 1/2020 | Han et al. | |
| 10,561,563 B2 | 2/2020 | Herr et al. | |
| 10,576,620 B1 | 3/2020 | Chou et al. | |
| 11,413,210 B2 | 8/2022 | Contreras-Vidal et al. | |
| 2006/0184280 A1 | 8/2006 | Oddsson et al. | |
| 2007/0225620 A1 | 9/2007 | Carignan et al. | |
| 2009/0030530 A1 | 1/2009 | Martin | |
| 2009/0210093 A1 | 8/2009 | Jacobsen et al. | |
| 2010/0198124 A1 | 8/2010 | Bhugra | |
| 2010/0231206 A1 | 9/2010 | Kobayashi | |
| 2011/0066088 A1 | 3/2011 | Little et al. | |
| 2012/0089063 A1* | 4/2012 | Olson | A61H 9/0078 601/152 |
| 2012/0256381 A1 | 10/2012 | Bradshaw | |
| 2012/0289870 A1 | 11/2012 | Hsiao-Wecksler et al. | |
| 2013/0090580 A1 | 4/2013 | Hong et al. | |
| 2013/0226048 A1 | 8/2013 | Unluhisarcikli et al. | |
| 2013/0231595 A1* | 9/2013 | Zoss | A61H 1/0255 601/34 |
| 2014/0100494 A1 | 4/2014 | Sarkodie-Gyan et al. | |
| 2014/0330431 A1 | 11/2014 | Hollander et al. | |
| 2015/0141878 A1 | 5/2015 | Roy et al. | |
| 2015/0164731 A1 | 6/2015 | Kwak et al. | |
| 2015/0173993 A1 | 6/2015 | Walsh et al. | |
| 2015/0196403 A1 | 7/2015 | Kim et al. | |
| 2015/0257902 A1 | 9/2015 | Martin | |
| 2016/0107309 A1 | 4/2016 | Walsh et al. | |
| 2016/0143800 A1 | 5/2016 | Hyung et al. | |
| 2016/0278948 A1 | 9/2016 | Piercy et al. | |
| 2016/0331557 A1 | 11/2016 | Tong et al. | |
| 2016/0331624 A1 | 11/2016 | Sankai et al. | |
| 2017/0043482 A1 | 2/2017 | Hyun et al. | |
| 2017/0119132 A1 | 5/2017 | Pruess et al. | |
| 2017/0202724 A1 | 7/2017 | De Rossi et al. | |
| 2017/0354529 A1 | 12/2017 | Han et al. | |
| 2018/0104075 A1 | 4/2018 | Mooney et al. | |
| 2018/0116826 A1 | 5/2018 | Byars et al. | |
| 2018/0125738 A1 | 5/2018 | Witte et al. | |
| 2018/0177665 A1* | 6/2018 | Rogozinski | A61H 3/04 |
| 2018/0193172 A1 | 7/2018 | Smith et al. | |
| 2018/0200135 A1 | 7/2018 | Tung et al. | |
| 2018/0325764 A1* | 11/2018 | Yagi | B25J 11/009 |
| 2019/0011743 A1 | 1/2019 | Yan et al. | |
| 2019/0038448 A1 | 2/2019 | Choi et al. | |
| 2019/0070060 A1* | 3/2019 | Choi | G05D 17/02 |
| 2019/0083002 A1 | 3/2019 | Jang et al. | |
| 2019/0105215 A1 | 4/2019 | Dalley et al. | |
| 2019/0125004 A1 | 5/2019 | Thomas et al. | |
| 2019/0159728 A1 | 5/2019 | Pritchard et al. | |
| 2019/0159954 A1 | 5/2019 | Ozsecen et al. | |
| 2019/0160321 A1 | 5/2019 | Ozsecen et al. | |
| 2019/0175365 A1 | 6/2019 | Herr et al. | |
| 2019/0183713 A1 | 6/2019 | Sankai | |
| 2019/0254908 A1 | 8/2019 | Ortlieb et al. | |
| 2019/0254909 A1 | 8/2019 | Lee et al. | |
| 2019/0282429 A1 | 9/2019 | Son et al. | |
| 2019/0314185 A1 | 10/2019 | Yuge et al. | |
| 2019/0328552 A1 | 10/2019 | Herr et al. | |
| 2019/0328604 A1 | 10/2019 | Contreras-Vidal et al. | |
| 2019/0343707 A1 | 11/2019 | Riener et al. | |
| 2019/0343710 A1 | 11/2019 | Lerner | |
| 2019/0365554 A1 | 12/2019 | Davies-Sekle | |
| 2020/0011406 A1 | 1/2020 | Julin | |
| 2020/0016020 A1 | 1/2020 | Mooney et al. | |
| 2020/0018589 A1 | 1/2020 | Ausserlechner | |
| 2020/0093679 A1 | 3/2020 | Sonar et al. | |
| 2020/0197253 A1 | 6/2020 | Park et al. | |
| 2020/0253772 A1 | 8/2020 | Reid et al. | |
| 2020/0253774 A1 | 8/2020 | Pismennaya et al. | |
| 2020/0276698 A1 | 9/2020 | Ding et al. | |
| 2020/0326780 A1 | 10/2020 | Kearney et al. | |
| 2021/0085554 A1 | 3/2021 | Roh et al. | |
| 2021/0121355 A1 | 4/2021 | Behboodi et al. | |
| 2021/0290470 A1 | 9/2021 | Farris et al. | |
| 2021/0291355 A1 | 9/2021 | Lerner et al. | |
| 2021/0369536 A1 | 12/2021 | Mooney et al. | |
| 2021/0393467 A1 | 12/2021 | Ookoba | |
| 2022/0031552 A1 | 2/2022 | Mooney et al. | |

(56) References Cited

U.S. PATENT DOCUMENTS

| | | |
|---|---|---|
| 2022/0110814 A1 | 4/2022 | Mooney et al. |
| 2022/0273469 A1 | 9/2022 | Kazerooni et al. |

FOREIGN PATENT DOCUMENTS

| | | |
|---|---|---|
| CN | 105213153 B | 9/2015 |
| CN | 105213155 A | 1/2016 |
| CN | 103813772 B | 7/2016 |
| CN | 104644381 B | 8/2016 |
| CN | 104983543 B | 8/2016 |
| CN | 107115191 A | 9/2017 |
| CN | 209270231 U | 9/2017 |
| CN | 107874984 A | 4/2018 |
| CN | 105963100 B | 7/2018 |
| CN | 108283564 A | 7/2018 |
| CN | 108338896 A | 7/2018 |
| CN | 108451748 A | 8/2018 |
| CN | 106491319 B | 12/2018 |
| CN | 105456004 B | 2/2019 |
| CN | 109646245 A | 4/2019 |
| CN | 209107991 U | 7/2019 |
| CN | 110327189 A | 10/2019 |
| CN | 110478191 A | 11/2019 |
| CN | 110575350 A | 12/2019 |
| EP | 2 621 413 B1 | 6/2014 |
| EP | 2 564 817 B1 | 1/2019 |
| IN | 201631013395 A | 10/2017 |
| JP | 5935177 B2 | 6/2016 |
| KR | 20140107029 A | 9/2014 |
| WO | WO-2016/182473 A1 | 1/2016 |
| WO | WO-2016/180073 A1 | 3/2016 |
| WO | WO-2018/023109 A1 | 7/2017 |
| WO | WO-2019/160532 A1 | 2/2018 |

OTHER PUBLICATIONS

International Preliminary Report on Patentability on PCT Appl. Ser. No. PCT/US2021/034086 dated Dec. 15, 2022 (10 pages).
International Preliminary Report on Patentability on PCT Appl. Ser. No. PCT/US2021/034163 dated Dec. 15, 2022 (6 pages).
International Preliminary Report on Patentability on PCT Appl. Ser. No. PCT/US2021/034182 dated Dec. 15, 2022 (5 pages).
International Preliminary Report on Patentability on PCT Appl. Ser. No. PCT/US2021/034252 dated Dec. 15, 2022 (14 pages).
Pirjade et al., "Design and Fabrication of a Low-cost Human Body Lower Limb Exoskeleton," IEEE, Apr. 16, 2020, pp. 32-37.
Sanz-Morere et al., "A Knee-Ankle-Foot Orthosis to Assist the Sound Limb of Transfemoral Amputees," IEEE, vol. 1, No. 1, Feb. 13, 2019, pp. 38-48.
U.S. Non-Final Office Action on U.S. Appl. No. 17/504,261 dated Dec. 20, 2022 (9 pages).
U.S. Non-Final Office Action on U.S. Appl. No. 17/526,454 dated Jan. 12, 2023 (22 pages).
U.S. Notice of Allowance on U.S. Appl. No. 17/136,333 dated Apr. 6, 2022 (13 pages).
Xie et al., "An Unpowered Flexible Lower Limb Exoskeleton: Walking Assisting and Energy Harvesting," IEEE, vol. 24, No. 5, Oct. 5, 2019, pp. 2236-2247.
Zhou et al., "Preliminary Evaluation of Gait Assistance During Treadmill Walking with a Light-weight Bionic Knee Exoskeleton," IEEE, Dec. 7, 2016, pp. 1173-1178.
U.S. Corrected Notice of Allowance on U.S. Appl. No. 17/504,261 dated Apr. 24, 2023 (2 pages).
U.S. Notice of Allowance on U.S. Appl. No. 17/526,454 dated Apr. 26, 2023 (8 pages).
International Search Report and Written Opinion for PCT Appl. No. PCT/US2021/047252, dated Nov. 23, 2021.
U.S. Office Action on U.S. Appl. No. 17/136,333 dated Nov. 23, 2021.
Witte et al.: "Design of Two Lightweight, High-Bandwidth Torque-Controlled Ankle Exoskeletons" IEEE International Conference on Robotics and Automation (ICRA); May 2015.
Zhang et al.: "Experimental comparison of torque control methods on an ankle exoskeleton during human walking" IEEE International Conference on Robotics and Automation (ICRA); May 2015.
Dollar et al., Active Orthoses for the Lower-Limbs: Challenges and State of the Art, 2008, IEEE, p. 968-977 (Year: 2008).
Dollar et al., Lower Extremity Exoskeletons and Active Orthoses: Challenges and State-of-the-Art, 2008, IEEE, p. 144-158 (Year:2008).
Foreign Search Report on non-Foley case related to PCT PCT/US2021/034086 dated Jun. 28, 2021.
Foreign Search Report on PCT PCT/US2021/034163 dated Jun. 25, 2021.
Foreign Search Report on PCT PCT/US2021/034182 dated Jun. 29, 2021.
Foreign Search Report on PCT PCT/US2021/047295 dated Sep. 23, 2021.
Foreign Search Report on PCT PCT/US2021/34252 dated Jun. 28, 2021.
Goldfarb et al. Design of a Controlled-Brake Orthosis for FES-aided gait, 1996, IEEE, p. 13-24 (Year:1996).
Haque et al., Design and Preliminary Testing of an Insrumented Exoskeleton for Walking Gait Measurement, 2019, IEEE, 2019, 6 pages.
International Search Report and Written Opinion on PCT/US2020/059866 dated Feb. 4, 2021, 8 pages.
Kim et al., Mechanical Design of the Hanyang Exoskeleton Assistive Robot (HEXAR), 2014, IEEE, 479-484 (Year: 2014).
Non-Final Office Action on U.S. Appl. No. 17/028,761 dated Oct. 12, 2021.
Notice of Allowance on U.S. Appl. No. 17/022,982 dated Jan. 29, 2021.
Notice of Allowance on U.S. Appl. No. 17/084,111 dated Feb. 19, 2021.
Notice of Allowance on U.S. Appl. No. 17/084,111 dated May 20, 2021.
Notice of Allowance on U.S. Appl. No. 17/109,911 dated Feb. 3, 2021.
U.S. Non-Final Office Action on U.S. Appl. No. 17/028,761 dated Nov. 23, 2020.
U.S. Notice of Allowance on U.S. Appl. No. 17/022,982 dated Sep. 27, 2021, 9 pages.
U.S. Notice of Allowance on U.S. Appl. No. 17/109,911 dated Sep. 14, 2021, 5 pages.
U.S. Notice of Allowance on U.S. Appl. No. 17/109,911 dated May 25, 2021.
U.S. Notice of Allowance on U.S. Appl. No. 17/084,111 dated Sep. 17, 2021, 7 pages.
U.S. Office Action on U.S. Appl. No. 17/022,982 dated May 4, 2021.
U.S. Office Action on U.S. Appl. No. 17/028,761 dated Mar. 16, 2021, 18 pages.
U.S. Office Action on U.S. Appl. No. 17/136,333 dated Mar. 12, 2021, 24 pages.
U.S. Office Action on U.S. Appl. No. 17/136,333 dated Jun. 21, 2021.
International Preliminary Report on Patentability on PCT Appl. Ser. No. PCT/US2021/047252 dated Mar. 9, 2023 (9 pages).
International Preliminary Report on Patentability on PCT Appl. Ser. No. PCT/US2021/047295 dated Mar. 30, 2023 (5 pages).
U.S. Final Office Action on U.S. Appl. No. 17/526,454 dated Apr. 7, 2023 (6 pages).
U.S. Notice of Allowance on U.S. Appl. No. 17/504,261 dated Apr. 7, 2023 (9 pages).
U.S. Notice of Allowance on U.S. Appl. No. 17/028,761 dated Feb. 2, 2022.
U.S. Non-Final Office Action on U.S. Appl. No. 17/867,162 dated Apr. 12, 2023 (32 pages).
U.S. Non-Final Office Action on U.S. Appl. No. 17/002,556 dated Aug. 21, 2023 (107 pages).
U.S. Notice of Allowance on U.S. Appl. No. 17/867,162 dated Aug. 30, 2023 (17 pages).

(56) References Cited

OTHER PUBLICATIONS

EP Office Action on EP Appl. Ser. No. 20888375.1 dated Sep. 14, 2023 (7 pages).
U.S. Notice of Allowance on U.S. Appl. No. 17/867,162 dated Oct. 5, 2023 (18 pages).

* cited by examiner

SYSTEMS AND METHODS FOR BILATERAL WIRELESS COMMUNICATION

CROSS-REFERENCES TO RELATED APPLICATIONS

This application claims the benefit of priority under 35 U.S.C. § 120 as a continuation of U.S. patent application Ser. No. 17/084,111, filed Oct. 29, 2021, which claims the benefit of priority under 35 U.S.C. § 119 to U.S. Provisional Patent Application No. 63/034,748, filed Jun. 4, 2020, each of which is hereby incorporated herein by reference in its entirety.

TECHNICAL FIELD

This disclosure generally relates to the field of exoskeletons.

BACKGROUND

Exoskeletons can be worn by a user to facilitate movement of limbs of the user.

SUMMARY

Systems, methods and devices of this technical solution are directed to bilateral wireless communication between multiple exoskeleton devices. An exoskeleton device, such as but not limited to, an exoskeleton boot can be worn by a user on each lower limb (e.g., right leg, left leg) to aid the user in performing movements and/or activities (e.g., walking, running, hiking). The exoskeleton boots can provide force or torque to the respective limb to reduce an amount of force provided by the user to perform the movement and reduce a physiological impact on the user during the movement. The exoskeleton devices can communicate during the movements performed by the user while wearing the respective exoskeleton devices to provide user feedback and modify control parameters of the exoskeleton devices. For example, the exoskeleton devices can include or connect to a plurality of sensors that monitor and record measurements (e.g., gait state, joint angles, speed, body positioning) of the user during the movement. The sensor data can be used to calculate force or torque provided by an exoskeleton device at any given time such as during the movement and/or for one or more subsequent movements. The exoskeleton devices can communicate to share the sensor data to provide increased control capability of the exoskeleton devices and increased performance of the user during the movement. However, communications between the exoskeleton devices can become delayed or lost during the movements. The systems and methods described herein can include multi-control strategies that use real-time latency measurements to determine a control strategy and reduce the need for communication between the exoskeleton devices to be always available.

At least one aspect of the present disclosure is directed to a method for communicating between multiple lower limb exoskeletons. The method can include receiving, by a first exoskeleton boot responsive to transmitting a first packet, a second packet from a second exoskeleton boot through a wireless connection between the first exoskeleton boot and the second exoskeleton boot. The method can include determining, by the first exoskeleton boot, a latency for communication between the first exoskeleton boot and the second exoskeleton boot based on a time difference between transmission of the first packet and receipt of the second packet. The method can include updating, responsive to the comparison, a model indicating data weighted based on the latency for controlling the first exoskeleton boot and the second exoskeleton boot. The method can include generating, using data from the model, a command to cause an electric motor of the first exoskeleton boot to generate torque to aid a limb of a user in performing a movement.

In embodiments, the method can include determining, by the first exoskeleton boot responsive to a comparison of the latency to a threshold, whether to accept or reject the second packet from the second exoskeleton boot. The method can include selecting, by the first exoskeleton boot responsive to the comparison, a state of communication between the first exoskeleton boot and the second exoskeleton boot. The method can include accepting, by the first exoskeleton boot based on the selected state, data from the second packet. The method can include selecting, by the first exoskeleton boot responsive to the comparison, a state of communication between the first exoskeleton boot and the second exoskeleton boot. The method can include rejecting, by the first exoskeleton boot based on the selected state, data from the second packet.

The method can include modifying, by the first exoskeleton boot, the threshold based on a type of activity represented by data of the second packet. The method can include modifying, by the first exoskeleton boot, the threshold based on a type of gait event associated with data of the second packet. The method can include determining, by the first exoskeleton boot, a confidence factor for the second packet based on a time difference between the second packet and one or more previous packets accepted from the second exoskeleton boot. The method can include transitioning, by the first exoskeleton boot using data from the second packet, from a first state to a second state. The method can include performing, by the first exoskeleton boot responsive to data from the second packet, a gait event using the first exoskeleton boot and the second exoskeleton boot.

In embodiments, the method can include initiating, by the first exoskeleton boot, a timer responsive to transmitting the first packet to the second exoskeleton boot. The method can include stopping, by the first exoskeleton boot, the timer responsive to receiving the second packet from the second exoskeleton boot. The method can include determining, by the first exoskeleton boot, the latency for communication between the first exoskeleton boot and the second exoskeleton boot based on a value of the timer. In embodiments, the second packet can include data associated with at least one of: a gait event, state information, movement information, sensor data, or measurement data.

In at least one aspect, a system for communicating between multiple lower limb exoskeletons is provided. The system can include a first exoskeleton boot comprising a processor coupled to a memory. The first exoskeleton boot can be configured to receive, responsive to transmitting a first packet, a second packet from a second exoskeleton boot through a wireless connection between the first exoskeleton boot and the second exoskeleton boot. The first exoskeleton boot can be configured to determine a latency for communication between the first exoskeleton boot and the second exoskeleton boot based on a time difference between transmission of the first packet and receipt of the second packet. The first exoskeleton boot can be configured to update, responsive to the comparison, a model indicating data weighted based on the latency for controlling the first exoskeleton boot and the second exoskeleton boot. The first exoskeleton boot can be configured to generate, using data from the model, a command to cause an electric motor of the first exoskeleton boot to generate torque to aid a limb of a user in performing a movement.

In embodiments, the first exoskeleton boot can be configured to determine, responsive to a comparison of the latency to a threshold, whether to accept or reject the second packet from the second exoskeleton boot. The first exoskeleton boot can be configured to select, responsive to the comparison, a state of communication between the first exoskeleton boot and the second exoskeleton boot. The first exoskeleton boot can be configured to accept, based on the selected state, data from the second packet. The first exoskeleton boot can be configured to select, responsive to the comparison, a state of communication between the first exoskeleton boot and the second exoskeleton boot. The first exoskeleton boot can be configured to reject, based on the selected state, data from the second packet. The first exoskeleton boot can be configured to modify the threshold based on a type of activity represented by data of the second packet.

In embodiments, the first exoskeleton boot can be configured to modify the threshold based on a type of gait event associated with data of the second packet. The first exoskeleton boot can be configured to determine a confidence factor for the second packet based on a time difference between the second packet and one or more previous packets accepted from the second exoskeleton boot. The first exoskeleton boot can be configured to transition, using data from the second packet, from a first state to a second state. The first exoskeleton boot can be configured to perform, responsive to data from the second packet, a gait event using the first exoskeleton boot and the second exoskeleton boot.

The first exoskeleton boot can be configured to initiate a timer responsive to transmitting the first packet to the second exoskeleton boot. The first exoskeleton boot can be configured to stop the timer responsive to receiving the second packet from the second exoskeleton boot. The first exoskeleton boot can be configured to determine the latency for communication between the first exoskeleton boot and the second exoskeleton boot based on a value of the timer. In embodiments, the second packet can include data associated with at least one of: a gait event, state information, movement information, sensor data, or measurement data.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

The details of one or more implementations of the subject matter described in this specification are set forth in the accompanying drawings and the description below. Other features, aspects, and advantages of the subject matter will become apparent from the description, the drawings, and the claims.

Like reference numbers and designations in the various drawings indicate like elements.

DETAILED DESCRIPTION

This disclosure relates generally to performance enhancing wearable technologies. Particularly, this disclosure relates to apparatuses, systems, and methods for an active exoskeleton with a local battery. The local battery can include an onboard power source that is used to power electronics and one or more actuators.

I. Exoskeleton Overview

Exoskeletons (e.g., battery-powered active exoskeleton, battery-powered active exoskeleton boot, lower limb exoskeleton, knee exoskeleton, or back exoskeleton) can include devices worn by a person to augment physical abilities. Exoskeletons can be considered passive (e.g., not requiring an energy source such as a battery) or active (e.g., requiring an energy source to power electronics and usually one or many actuators). Exoskeletons may be capable of providing large amounts of force, torque and/or power to the human body in order to assist with motion.

Exoskeletons can transfer energy to the user or human. Exoskeletons may not interfere with the natural range of motion of the body. For example, exoskeletons can allow a user to perform actions (e.g., walking, running, reaching, or jumping) without hindering or increasing the difficulty of performing these actions. Exoskeletons can reduce the difficulty of performing these actions by reducing the energy or effort the user would otherwise exert to perform these actions. Exoskeletons can convert the energy into useful mechanical force, torque, or power. Onboard electronics (e.g., controllers) can control the exoskeleton. Output force and torque sensors can also be used to make controlling easier.

Figure 1:
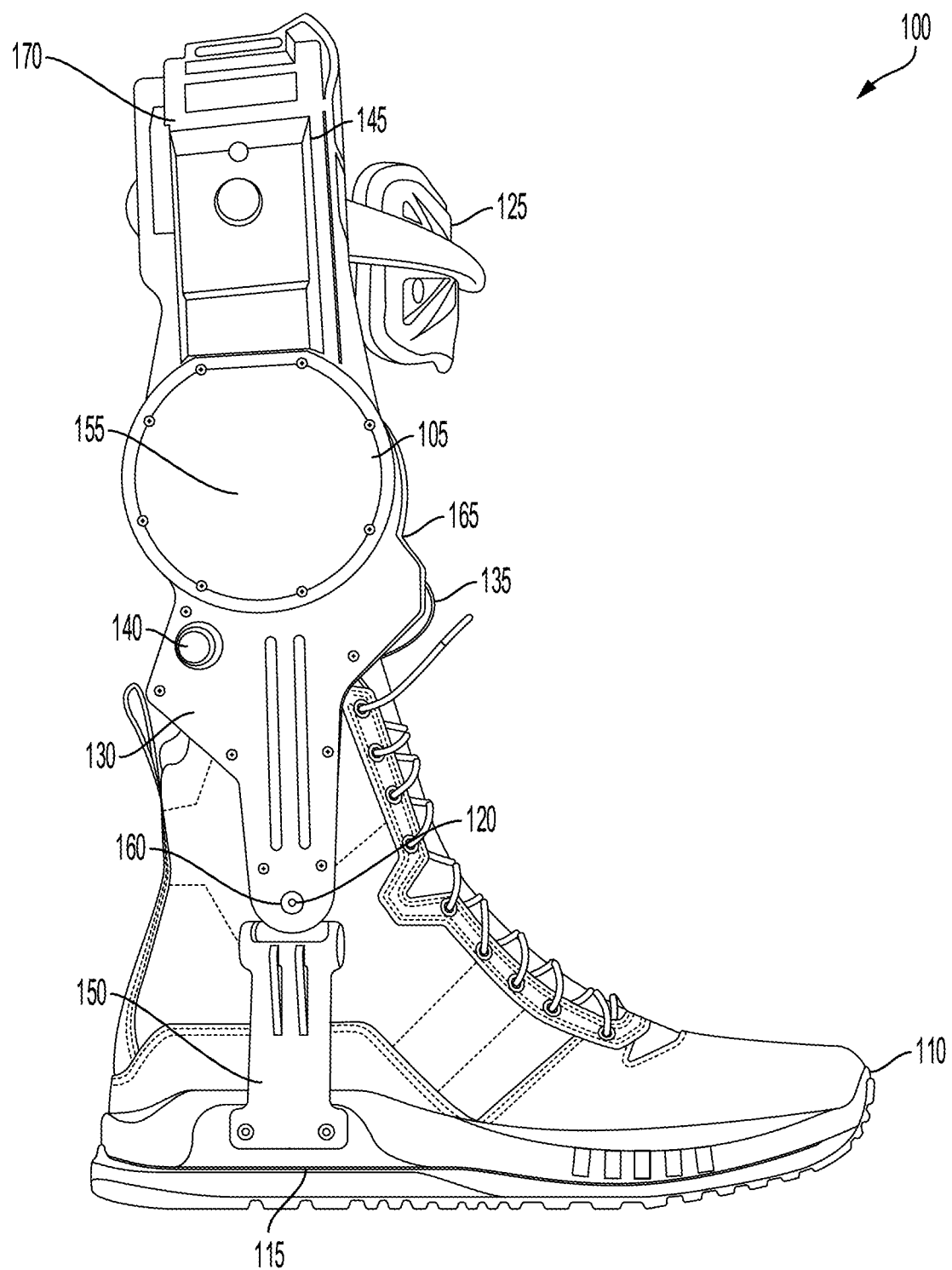
FIG. 1 illustrates a schematic diagram of an exoskeleton, according to an embodiment.

FIG. 1 illustrates a schematic diagram of an exoskeleton 100. The exoskeleton 100 can be referred to as a lower limb exoskeleton, lower limb exoskeleton assembly, lower limb exoskeleton system, ankle exoskeleton, ankle foot orthosis, knee exoskeleton, hip exoskeleton, exoskeleton boot, or exoboot. The exoskeleton 100 can include a water resistant active exoskeleton boot. For example, the exoskeleton 100 can resist the penetration of water into the interior of the exoskeleton 100. The exoskeleton 100 can include a water resistant active exoskeleton boot. For example, the exoskeleton 100 can be impervious to liquids (e.g., water) and non-liquids (e.g., dust, dirt, mud, sand, or debris). The exoskeleton 100 can remain unaffected by water or resist the ingress of water, such as by decreasing a rate of water flow into the interior of the exoskeleton 100 to be less than a target rate indicative of being water resistant or waterproof. For example, the exoskeleton 100 can operate in 3 feet of water for a duration of 60 minutes. The exoskeleton 100 can have an ingress protection rating (IP) rating of 68. The exoskeleton 100 can have a National Electrical Manufacturer Association (NEMA) rating of 4x, which can indicate that the exoskeleton 100 has a degree of protection with respect to harmful effects on the equipment due to the ingress of water (e.g., rain, sleet, snow, splashing water, and hose directed water), and that the exoskeleton can be undamaged by the external formation of ice on the enclosure.

The exoskeleton 100 can include a shin pad 125 (e.g., shin guard). The shin pad 125 can be coupled to a shin of a user below a knee of the user. The shin pad 125 can be coupled to the shin of the user to provide support. The shin pad 125 can include a piece of equipment to protect the user from injury. For example, the shin pad 125 can protect the lower extremities of the user from external impact. The shin pad 125 can interface with the shin of the user. The shin pad 125 can include a band (e.g., adjustable band) configured to wrap around the shin of the user. The shin pad 125 can secure the upper portion of the exoskeleton 100 to the body of the user. The shin pad 125 can secure or help secure the exoskeleton 100 to the shin, leg, or lower limb of the user. The shin pad 125 can provide structural integrity to the exoskeleton 100. The shin pad 125 can support other components of the exoskeleton 100 that can be coupled to the shin pad 125. The shin pad 125 can be made of lightweight, sturdy, and/or water resistant materials. For example, the shin pad 125 can be made of plastics, aluminum, fiberglass, foam rubber, polyurethane, and/or carbon fiber.

The exoskeleton 100 can include one or more housings 105. At least one of the one or more housings 105 can be coupled to the shin pad 125 below the knee of the user. The shin pad 125 can be coupled to the at least one housing via a shin lever. The shin lever can extend from the at least one housing to the shin pad 125. The shin lever can include a mechanical structure that connects the shin pad 125 to a chassis. The chassis can include a mechanical structure that connects static components.

The one or more housings 105 can enclose electronic circuitry (e.g., electronic circuitry 505). The one or more housings 105 can encapsulate some or all the electronics of the exoskeleton 100. The one or more housings 105 can include an electronics cover (e.g., case). The one or more housings 105 can enclose an electric motor (e.g., motor 330). The electric motor can generate torque about an axis of rotation of an ankle joint of the user. The ankle joint can allow for dorsiflexion and/or plantarflexion of the user's foot. The exoskeleton 100 can include an ankle joint component 120 that rotates about the axis of rotation the ankle joint. The ankle joint component 120 can be positioned around or adjacent to the ankle joint.

The exoskeleton 100 can include a rotary encoder 155 (e.g., shaft encoder, first rotary encoder, or motor encoder). The rotary encoder 155 can be enclosed within the one or more housings 105. The rotary encoder 155 can measure an angle of the electric motor. The angle of the electric motor can be used by the controller to determine an amount of torque applied by the exoskeleton 100. For example, the angle of the electric motor can correspond to an amount of torque applied by the exoskeleton 100. An absolute angle of the electric motor can correspond to an amount of torque applied by the exoskeleton 100. The rotary encoder 155 can include an inductive encoder. The ankle joint component 120 can be actuated by a motor (e.g., electric motor). The rotary encoder 155 can include a contactless magnetic encoder or an optical encoder.

The exoskeleton 100 can include a second rotary encoder 160 (e.g., ankle encoder). The second rotary encoder 160 can measure an angle of the ankle joint. The angle of the ankle joint can be used by the controller to determine an amount of torque applied by the exoskeleton 100. The second rotary encoder 160 can include a first component enclosed in the one or more housings 105 and in communication with the electronic circuitry 505. The second rotary encoder 160 can include a second component located outside the one or more housings 105 and configured to interact with the first component. The second rotary encoder 160 can include a contactless magnetic encoder, a contactless inductive encoder, or an optical encoder. The second rotary encoder 160 can detect the angle of the ankle joint while the rotary encoder 155 can detect the angle of the electric motor. The angle of the electric motor can be different from the angle of the ankle joint. The angle of the electric motor can be independent of the angle of the ankle joint. The angle of the ankle joint can be used to determine an output (e.g., torque) of the electric motor. The ankle joint component 120 can be coupled to the second rotary encoder 160.

The one or more housings 105 can encapsulate electronics that are part of the exoskeleton 100. The one or more housings 105 can form a fitted structure (e.g., clamshell structure) to enclose the electronic circuitry and the electric motor. The fitted structure can be formed from two or more individual components. The individual components of the fitted structure can be joined together to form a single unit. The one or more housings 105 can be formed of plastic or metal (e.g., aluminum). An adhesive sealant can be placed between individual components of the fitted structure and under the electronics cover. A gasket can be placed between individual components of the fitted structure and under the electronics cover. The gasket can be placed in the seam between the individual components of the fitted structure.

A sealant 165 can be placed in contact with the one or more housings 105 to close the one or more housings 105 and prevent an ingress of water into the one or more housings 105. The sealant 165 used to close the one or more housings 105 can include an adhesive sealant (e.g., super glue, epoxy resin, or polyvinyl acetate). The adhesive sealant can include a substance used to block the passage of fluids through the surface or joints of the one or more housings 105. The sealant 165 used to close the one or more housings 105 can include epoxy. The sealant 165 can permanently seal or close the one or more housings 105. For example, the sealant 165 can seal or close the one or more housings 105 such that the one or more housings are not removably attached to one another.

The exoskeleton 100 can couple with a boot 110. For example, the exoskeleton 100 can be attached to the boot 110. The boot 110 can be worn by the user. The boot 110 can be connected to the exoskeleton 100. The exoskeleton 100 can be compatible with different boot shapes and sizes.

The exoskeleton 100 can include an actuator 130 (e.g., actuator lever arm, or actuator module). The actuator 130 can include one or more of the components in the exoskeleton 100. For example, the actuator 130 can include the one or more housings 105, the footplate 115, the ankle joint component 120, the actuator belt 135, and the post 150, while excluding the boot 110. The boot 110 can couple the user to the actuator 130. The actuator 130 can provide torque to the ground and the user.

The exoskeleton 100 can include a footplate 115 (e.g., carbon insert, carbon shank). The footplate 115 can include a carbon fiber structure located inside of the sole of the boot 110. The footplate 115 can be made of a carbon-fiber composite. The footplate 115 can be inserted into the sole of the boot 110. The footplate 115 can be used to transmit torque from the actuator 130 to the ground and to the user. The footplate 115 can be located in the sole of the exoskeleton 100. This footplate 115 can have attachment points that allow for the connection of the exoskeleton's mechanical structure. An aluminum insert with tapped holes and cylindrical bosses can be bonded into the footplate 115. This can create a rigid mechanical connection to the largely compliant boot structure. The bosses provide a structure that can be used for alignment. The footplate 115 can be sandwiched between two structures, thereby reducing the stress concentration on the part. This design can allow the boot to function as a normal boot when there is no actuator 130 attached.

The exoskeleton 100 can include an actuator belt 135 (e.g., belt drivetrain). The actuator belt 135 can include a shaft that is driven by the motor and winds the actuator belt 135 around itself. The actuator belt 135 can include a tensile member that is pulled by the spool shaft and applies a force to the ankle lever. Tension in the actuator belt 135 can apply a force to the ankle lever. The exoskeleton 100 can include an ankle lever. The ankle lever can include a lever used to transmit torque to the ankle. The exoskeleton 100 can be used to augment the ankle joint.

The exoskeleton 100 can include a power button 140 (e.g., switch, power switch). The power button 140 can power the electronics of the exoskeleton 100. The power button 140 can be located on the exterior of the exoskeleton 100. The power button 140 can be coupled to the electronics in the interior of the exoskeleton 100. The power button 140 can be electrically connected to an electronic circuit. The power button 140 can include a switch configured to open or close the electronic circuit. The power button 140 can include a low-power, momentary push-button configured to send power to a microcontroller. The microcontroller can control an electronic switch.

The exoskeleton 100 can include a battery holder 170 (e.g., charging station, dock). The battery holder 170 can be coupled to the shin pad 125. The battery holder 170 can be located below the knee of the user. The battery holder 170 can be located above the one or more housings 105 enclosing the electronic circuitry. The exoskeleton 100 can include a battery module 145 (e.g., battery). The battery holder 170 can include a cavity configured to receive the battery module 145. A coefficient of friction between the battery module 145 and the battery holder 170 can be established such that the battery module 145 is affixed to the battery holder 170 due to a force of friction based on the coefficient of friction and a force of gravity. The battery module 145 can be affixed to the battery holder 170 absent a mechanical button or mechanical latch. The battery module 145 can be affixed to the battery holder 170 via a lock, screw, or toggle clamp. The battery holder 170 and the battery module 145 can be an integrated component (e.g., integrated battery). The integrated battery can be supported by a frame of the exoskeleton 100 as opposed to having a separated enclosure. The integrated battery can include a charging port. For example, the charging port can include a barrel connector or a bullet connector. The integrated battery can include cylindrical cells or prismatic cells.

The battery module 145 can power the exoskeleton 100. The battery module 145 can include one or more electrochemical cells. The battery module 145 can supply electric power to the exoskeleton 100. The battery module 145 can include a power source (e.g., onboard power source). The power source can be used to power electronics and one or more actuators. The battery module 145 can include a battery pack. The battery pack can be coupled to the one or more housings 105 below a knee of the user. The battery pack can include an integrated battery pack. The integrated battery pack can remove the need for power cables, which can reduce the snag hazards of the system. The integrated battery pack can allow the system to be a standalone unit mounted to the user's lower limb. The battery module 145 can include a battery management system 324 to perform various operations. For example, the system can optimize the energy density of the unit, optimize the longevity of the cells, and enforce safety protocols to protect the user.

The battery module 145 can include a removable battery. The battery module 145 can be referred to as a local battery because it is located on the exoboot 100 (e.g., on the lower limb or below the knee of the user), as opposed to located on a waist or back of the user. The battery module 145 can include a weight-mounted battery, which can refer to the battery being held in place on the exoboots 100 via gravity and friction, as opposed to a latching mechanism. The battery module 145 can include a water resistant battery or a waterproof battery. The exoskeleton 100 and the battery module 145 can include water resistant connectors.

The battery module 145 can include a high-side switch (e.g., positive can be interrupted). The battery module 145 can include a ground that is always connected. The battery module 145 can include light emitting diodes (LEDs). For example, the battery module 145 can include three LEDs used for a user interface. The LEDs can be visible from one lens so that the LEDs appear as one multicolor LED. The LEDs can blink in various patterns and/or colors to communicate a state of the battery module 145 (e.g., fully charged, partially charged, low battery, or error).

The exoskeleton 100 can include a post 150. The post 150 can include a mechanical structure that connects to the boot 110. The post 150 can couple the ankle joint component 120 with the footplate 115. The post 150 can be attached at a first end to the footplate 115. The post 150 can be attached at a second end to the ankle joint component 120. The post 150 can pivot about the ankle joint component 120. The post 150 can include a mechanical structure that couples the footplate 115 with the ankle joint component 120. The post 150 can include a rigid structure. The post 150 can be removably attached to the footplate 115. The post 150 can be removably attached to the ankle joint component 120. For example, the post 150 can be disconnected from the ankle joint component 120.

The exoskeleton 100 can include a rugged system used for field testing. The exoskeleton 100 can include an integrated ankle lever guard (e.g., nested lever). The exoskeleton 100 can include a mechanical shield to guard the actuator belt 135 and ankle lever transmission from the environment. The housing structure of the system can extend to outline the range of travel of the ankle lever (e.g., lever arm 1140) on the lateral and medial side.

II. Active Exoskeleton with Local Battery

Exoskeletons 100 can transform an energy source into mechanical forces that augment human physical ability. Exoskeletons 100 can have unique power requirements. For example, exoskeletons 100 can use non-constant power levels, such as cyclical power levels with periods of high power (e.g., 100 to 1000 Watts) and periods of low or negative power (e.g., 0 Watts). Peaks in power can occur once per gait cycle. Batteries configured to provide power to the exoskeleton 100 can be the source of various issues. For example, batteries located near the waist of a user can require exposed cables that extend from the battery to the lower limb exoskeleton. These cables can introduce snag hazards, make the device cumbersome, and add mass to the system. Additionally, long cables with high peak power can result in excess radio emissions and higher voltage drops during high current peaks. Thus, systems, methods and apparatus of the present technical solution provide an exoskeleton with a local battery that can perform as desired without causing snag hazards, power losses, and radio interference. Additionally, the battery can be located close to the knee such that the mass felt by the user is reduced as compared to a battery located close the foot of the user.

Figure 2:
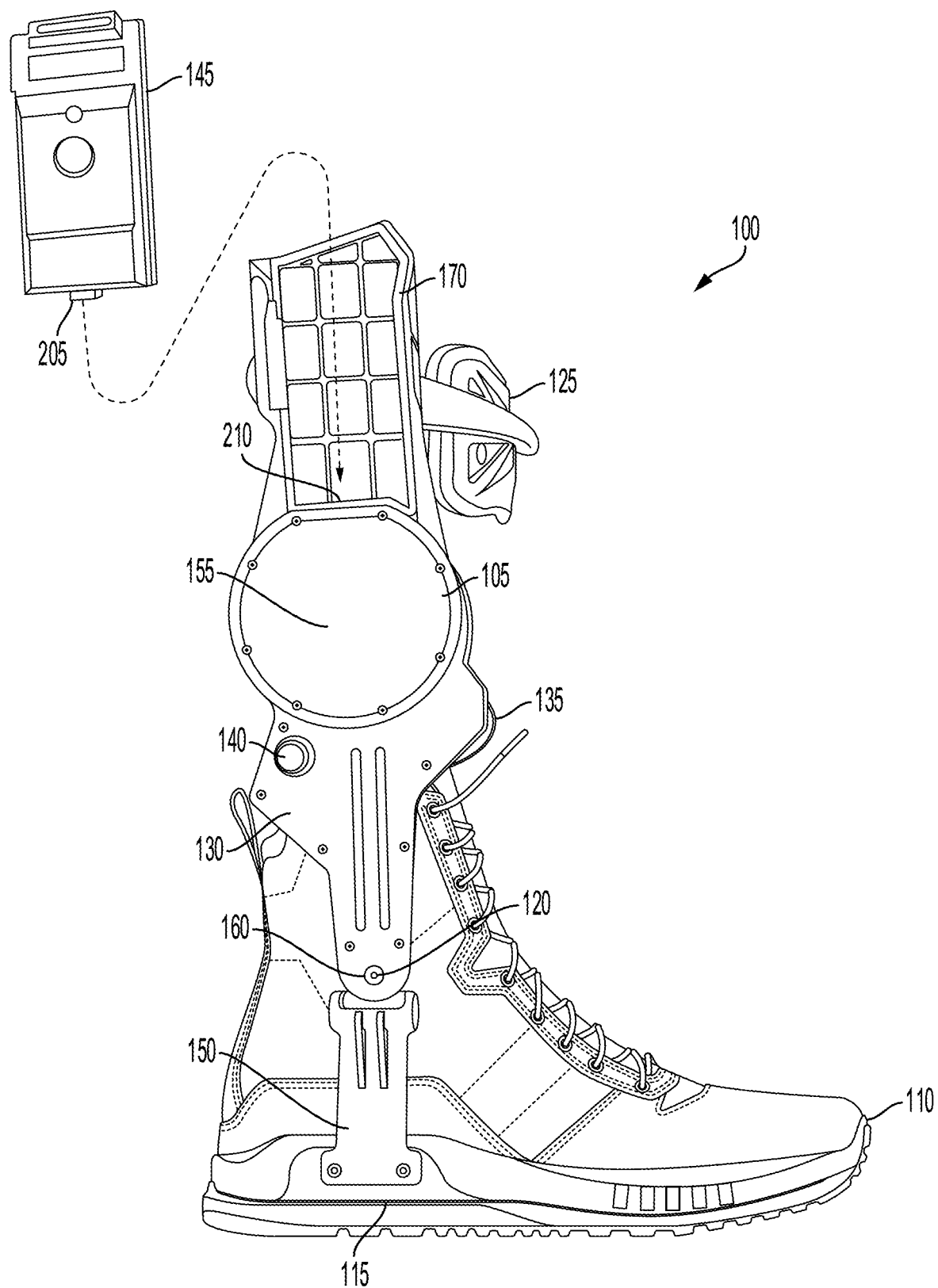
FIG. 2 illustrates a schematic diagram of an exoskeleton, according to an embodiment.

FIG. 2 illustrates a schematic diagram of the exoskeleton 100. The exoskeleton 100 includes the one or more housings 105, the boot 110 the footplate 115, the ankle joint component 120, shin pad 125, the actuator 130, the actuator belt 135, the power button 140, the battery module 145, the post 150, the rotary encoder 155, and the second rotary encoder 160. The battery module 145 can be inserted into the exoskeleton 100. The battery module 145 can include a sealed battery. The battery module 145 can coupled with the exoskeleton 100 via a waterproof or water resistant connection. The battery module 145 can connect locally (e.g., proximate) to the exoskeleton 100 such that a wire is not needed to run from the battery module 145 to the electronics.

The battery module 145 can be removably affixed to the battery holder 170. For example, the battery module 145 can slide in and out of the battery holder 170. By removably affixing the battery module 145 to the battery holder 170, the battery module 145 can be replaced with another battery module 145, or the battery module 145 can be removed for charging. The battery module 145 can include a first power connector 205 that electrically couples to a second power connector 210 located in the battery holder 170 while attached to the battery holder 170 to provide electric power to the electronic circuitry and the electric motor. The first power connector 205 and the second power connector 210 can couple (e.g., connect) the battery module 145 with the electronic circuitry. The first power connector 205 and the second power connector 210 can couple the battery module 145 with the one or more housings 105. The first power connector 205 can be recessed in the battery module 145 to protect the first power connector 205 from loading and impacts. The first power connector 205 and the second power connector 210 can include wires (e.g., two wires, three wires, or four wires). The battery module 145 can communicate with the electronic circuitry via the first power connector 205 and the second power connector 210. The first power connector 205 and the second power connector 210 can include an exposed connector.

The geometry of the battery module 145 can allow for storage and packing efficiency. The battery module 145 can include a gripping element to allow for ergonomic ease of removal and insertion of the battery module 145 into the battery holder 170. The battery module 145 can be made of lightweight plastics or metals. The battery module 145 can be made of heat insulating materials to prevent heat generated by the battery cells 305 from reaching the user. One or more faces of the battery module 145 can be made of metal to dissipate heat.

The exoskeleton 100 can communicate with the battery module 145 during operation. The exoskeleton 100 can use battery management system information to determine when safety measures will trigger. For example, during a high current peak (e.g., 15 A) or when the temperature is near a threshold, the power output can be turned off. The exoskeleton 100 can temporarily increase safety limits for very specific use cases (e.g., specific environmental conditions, battery life). The battery module 145 can prevent the exoskeleton 100 from shutting down by going into a low power mode and conserving power. The exoskeleton 100 can put the battery module 145 in ship mode if a major error is detected and the exoskeleton 100 wants to prevent the user from power cycling. The battery management system 324 can be adapted to support more or less series cells, parallel cells, larger capacity cells, cylindrical cells, different lithium chemistries, etc.

Figure 3:
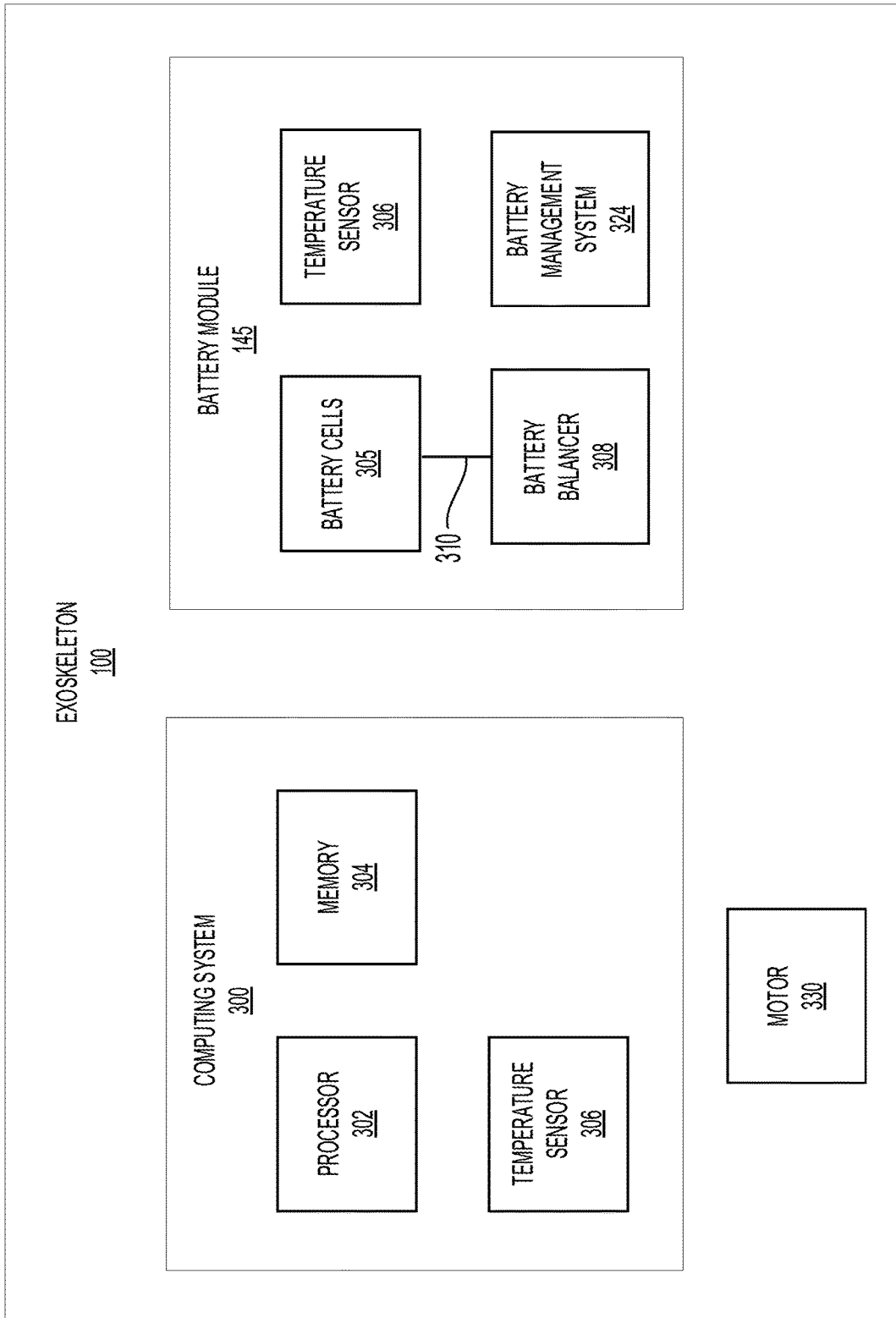
FIG. 3 illustrates a schematic diagram of an exoskeleton, according to an embodiment.

FIG. 3 illustrates a schematic diagram of an exoskeleton 100. The exoskeleton 100 can include a motor 330. The motor 330 can generate torque about an axis of rotation of an ankle joint of the user. The exoskeleton 100 can include the battery module 145. The exoskeleton 100 can include a computing system 300. The exoskeleton 100 can include one or more processors 302, memory 304, and one or more temperature sensors 306 (e.g., thermocouples). The one or more processors 302, memory 304, and one or more temperature sensor 306 can be located within the computing system 300. In some cases, the computing system 300 can include the batter balancer 308 as opposed to the battery module 145.

The one or more processors 302 can receive data corresponding to a performance of the battery module 145. The data can include one or more of a temperature, current, voltage, battery percentage, internal state or firmware version. The one or more processors 302 can determine, based on a safety policy, to trigger a safety action. The safety policy can include triggering the safety action if a threshold temperature, voltage or battery percentage is crossed. For example, the safety policy can include triggering the safety action if a temperature of one or more of the plurality of battery cells 305 is higher than a threshold temperature. The safety policy can include triggering the safety action if a battery percentage of the battery module 145 is below a threshold battery percentage. The safety policy can include triggering the safety action if a measured temperature is higher than the threshold temperature. The measured temperature can include the temperature of the printed circuit board and battery cells 305. The measured temperature can include the temperature of the printed circuit board and battery cells 305 measured in two locations. The safety policy can include triggering the safety action if a measured voltage is higher than the threshold voltage.

The one or more processors 302 can instruct, based on the safety action, the electronic circuitry to adjust delivery of power from the battery module 145 to the electric motor to reduce an amount of torque generated about the axis of rotation of the ankle joint of the user. The safety action can include lowering or reducing the amount of torque generated about the axis of rotation of the ankle joint of the user. The safety action can include increasing the amount of torque generated about the axis of rotation of the ankle joint of the user.

The one or more temperature sensors 306 can be placed between the plurality of battery cells 305 to provide an indication of a temperature between the plurality of battery cells 305. A temperature sensor of the one or more temperature sensors 306 can be mounted on the printed circuit board to measure a temperature of the printed circuit board. The electronic circuitry 505 can control the delivery of power from the battery module 145 to the electric motor based at least in part on the indication of the temperature between the plurality of battery cells 305 or the temperature of the printed circuit board.

The one or more battery balancers 308 can be configured to actively transfer energy from a first battery cell 305 of the plurality of battery cells 305 to a second battery cell 305 of the plurality of battery cells 305 having less charge than the first battery cell 305. A signal trace 310 can electrically connect the plurality of battery cells 305 to the one or more battery balancers 308. The signal trace 310 can be located on the printed circuit board.

The exoskeleton 100 can include the battery module 145. The battery module 145 can include a plurality of battery cells 305, one or more temperature sensors 306, one or more battery balancers 308, and a battery management system 324. The battery management system 324 can perform various operations. For example, the battery management system 324 can optimize the energy density of the unit, optimize the longevity of the cells 305, and enforce the required safety to protect the user. The battery management system 324 can go into ship mode by electrically disconnecting the battery module 145 from the rest of the system to minimize power drain while the system is idle. The battery management system 324 can go into ship mode if a major fault is detected. For example, if one or more of the plurality of battery cells 305 self-discharge at a rate higher than a threshold, the battery management system 324 can re-enable the charging port.

While these components are shown as part of the exoskeleton 100, they can be located in other locations such as external to the exoskeleton 100. For example, the battery management system 324 or the computing system 300 can be located external to the exoskeleton 100 for testing purposes.

Figure 4:
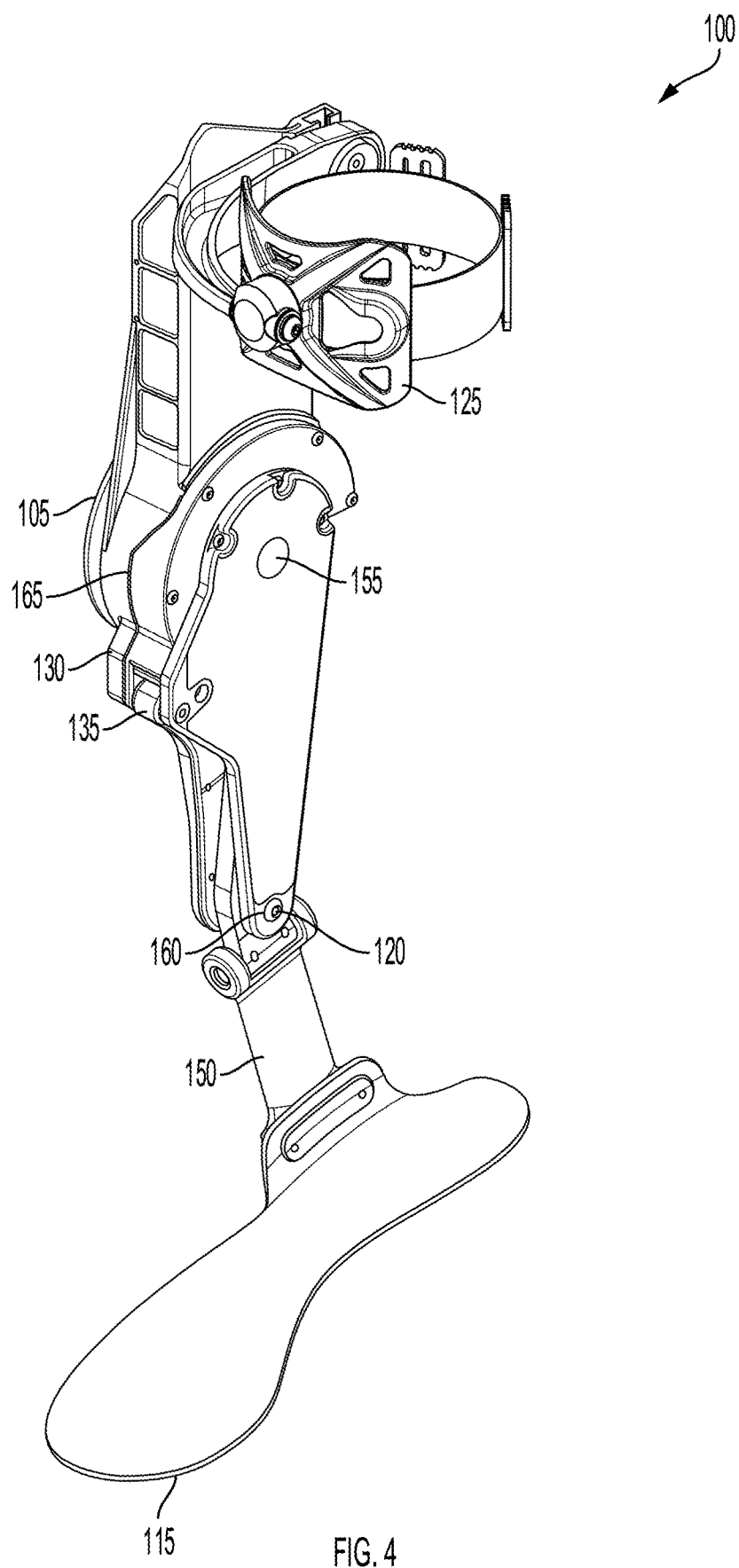
FIG. 4 illustrates a schematic diagram of an exoskeleton, according to an embodiment.

FIG. 4 illustrates a schematic diagram of the exoskeleton 100. The exoskeleton 100 can include the one or more housings 105, the footplate 115, the ankle joint component 120, shin pad 125, the actuator 130, the actuator belt 135, the post 150, the rotary encoder 155, the second rotary encoder 160, and the sealant 165 as described above. The one or more housings 105 can be coupled to the shin pad 125. The post 150 can couple the ankle joint component 120 with the footplate 115. The actuator 130 can include the one or more housings 105, the footplate 115, the ankle joint component 120, the actuator belt 135, and the post 150. The rotary encoder 155 can measure an angle of the electric motor. The second rotary encoder 160 can measure an angle of the ankle joint. The sealant 165 can be placed in contact with the one or more housings 105 to close the one or more housings 105 and prevent an ingress of water into the one or more housings 105.

Figure 5:
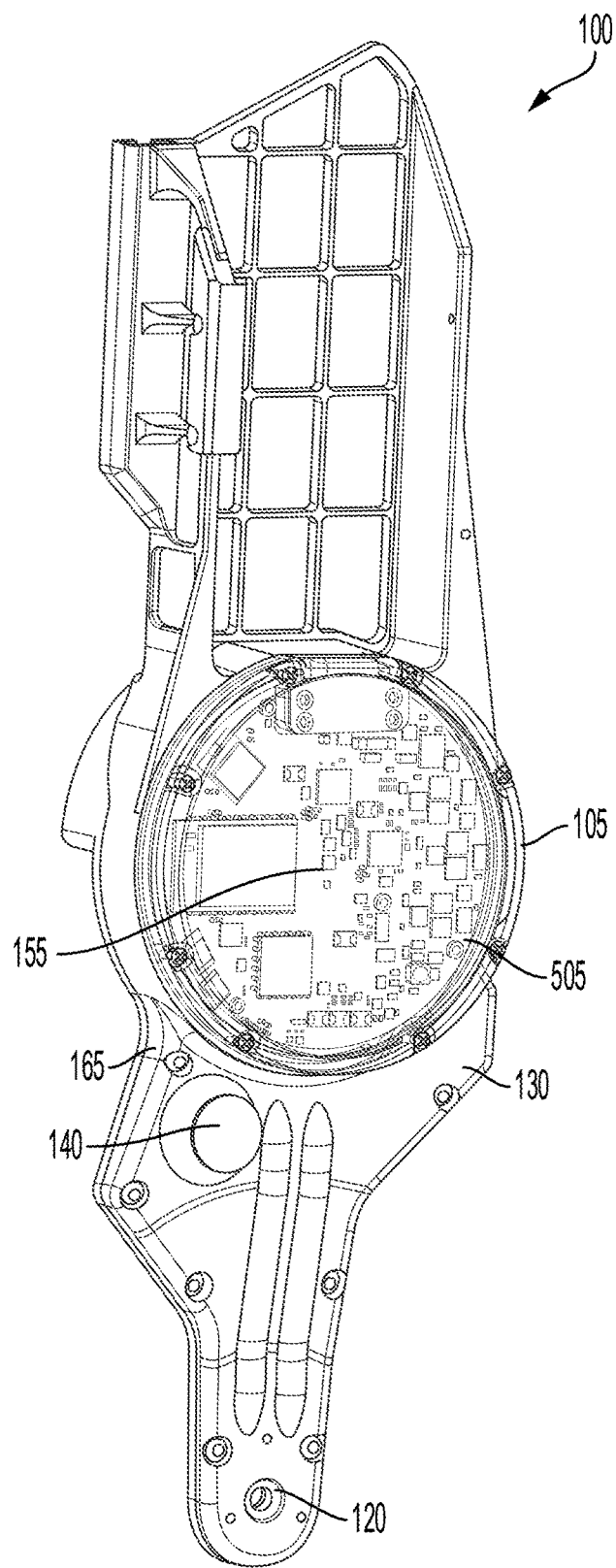
FIG. 5 illustrates a schematic diagram of the exoskeleton and internal parts, according to an embodiment.

FIG. 5 illustrates a schematic diagram of the exoskeleton 100 and internal parts. The exoskeleton 100 can include the one or more housings 105, the ankle joint component 120, the actuator 130, the power button 140, the rotary encoder 155, the second rotary encoder 160, and the sealant 165 as described above. The internal parts can include electronic circuitry 505 (e.g., electronic circuit, circuitry, electronics). The electronic circuitry 505 can include individual electronic components (e.g., resistors, transistors, capacitors, inductors, diodes, processors, or controllers). The power button 140 can be electrically connected to the electronic circuitry 505. The electronic circuitry 505 can be located behind the electric motor. The electronic circuitry 505 can include the main electronics board. The rotary encoder 155 can be located between the motor and electronic circuitry 505. The electronic circuitry 505 can control delivery of power from the battery module 145 to the electric motor to generate torque about the axis of rotation of the ankle joint of the user.

Figure 6:
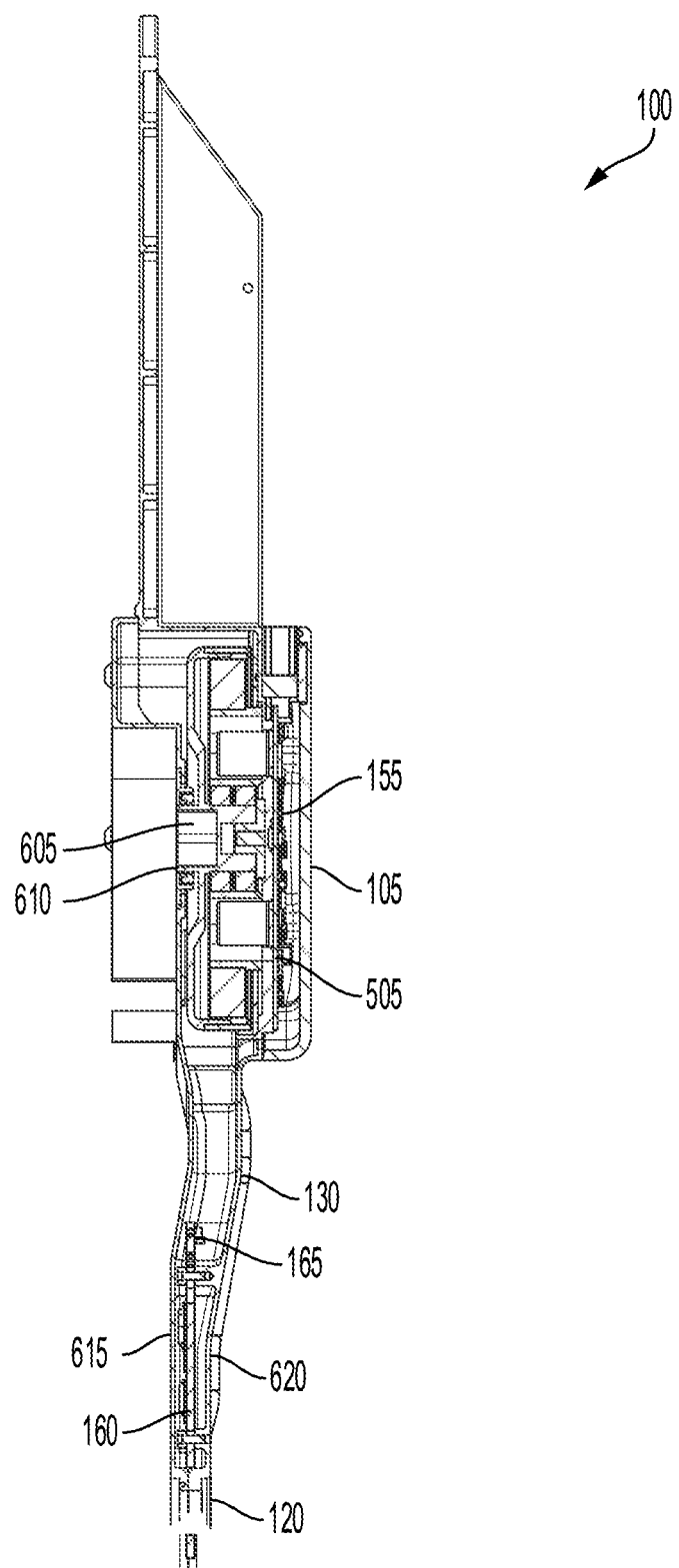
FIG. 6 illustrates a side view of an exoskeleton, according to an embodiment.

FIG. 6 illustrates a side view of the exoskeleton 100. The exoskeleton 100 can include the one or more housings 105, ankle joint component 120, the actuator 130, the rotary encoder 155, the second rotary encoder 160, the sealant 165, and electronic circuitry 505 as described above. The exoskeleton 100 can include an output shaft 605 (e.g., motor rotor, spool shaft, pinion gear, spur gear, or toothed pulley). The output shaft 605 can be coupled to the electric motor. The output shaft 605 can extend through a bore 610 in a housing of the one or more housings 105 enclosing the electric motor. The bore 610 can receive the output shaft 605. An encoder chip can be located on the electronics board on a first side of the electric motor. The encoder chip can measure the angular position of the rotary encoder 155. The exoskeleton 100 can include a transmission (e.g., gearbox) configured to couple the output shaft 605 to the electric motor. The transmission can include a machine in a power transmission system. The transmission can provide controlled application of power. The output shaft 605 can be integrated into the motor rotor. The output shaft 605 can be part of a mechanism (e.g., gears, belts, linkage, or change). An ankle shaft can extend through the second rotary encoder 160 which can increase the structural integrity of the exoskeleton 100.

The exoskeleton 100 can include a first component of the fitted structure 615 (e.g., first clamshell structure). The exoskeleton 100 can include a second component of the fitted structure 620 (e.g., second clamshell structure). The first component of the fitted structure 615 can be coupled with the second component of the fitted structure 620. The first component of the fitted structure 615 can be attached to the second component of the fitted structure 620 via the sealant 165 (e.g., adhesive sealant). The first component of the fitted structure 615 can be coupled to the second component of the fitted structure 620 such that the fitting prevents or decreases a rate of water flow into the interior of the exoskeleton 100. The fitted structure can include two or more components such that the assembly components prevents or decreases a rate of water flow into the interior of the exoskeleton 100. The first component of the fitted structure 615 and the second component of the fitted structure 620 can be stationary components. The number of individual components of the fitted structure can be minimized to decrease the number of possible entry points for water to enter the exoskeleton 100. The possible entry points can include seams and/or moving parts of the exoskeleton 100. The seams can be permanently sealed via the sealant 165.

An adhesive sealant (e.g., super glue, epoxy resin, or polyvinyl acetate) can be placed between the first component of the fitted structure 615 and the second component of the fitted structure 620. The adhesive sealant can prevent or decrease the rate of water flow through the seam between the first component of the fitted structure 615 and the second component of the fitted structure 620 into the interior of the exoskeleton 100. The adhesive sealant can be placed under the electronics cover. The adhesive sealant can prevent or decrease the rate of water flow through the seam between the electronics cover and the exoskeleton one or more housings 105 into the interior of the exoskeleton 100.

A gasket can be placed between the first component of the fitted structure 615 and the second component of the fitted structure 620. The gasket can be placed in the seam between the first component of the fitted structure 615 and the second component of the fitted structure 620. The gasket can prevent or decrease the rate of water flow through the seam between the first component of the fitted structure 615 and the second component of the fitted structure 620.

Figure 7:
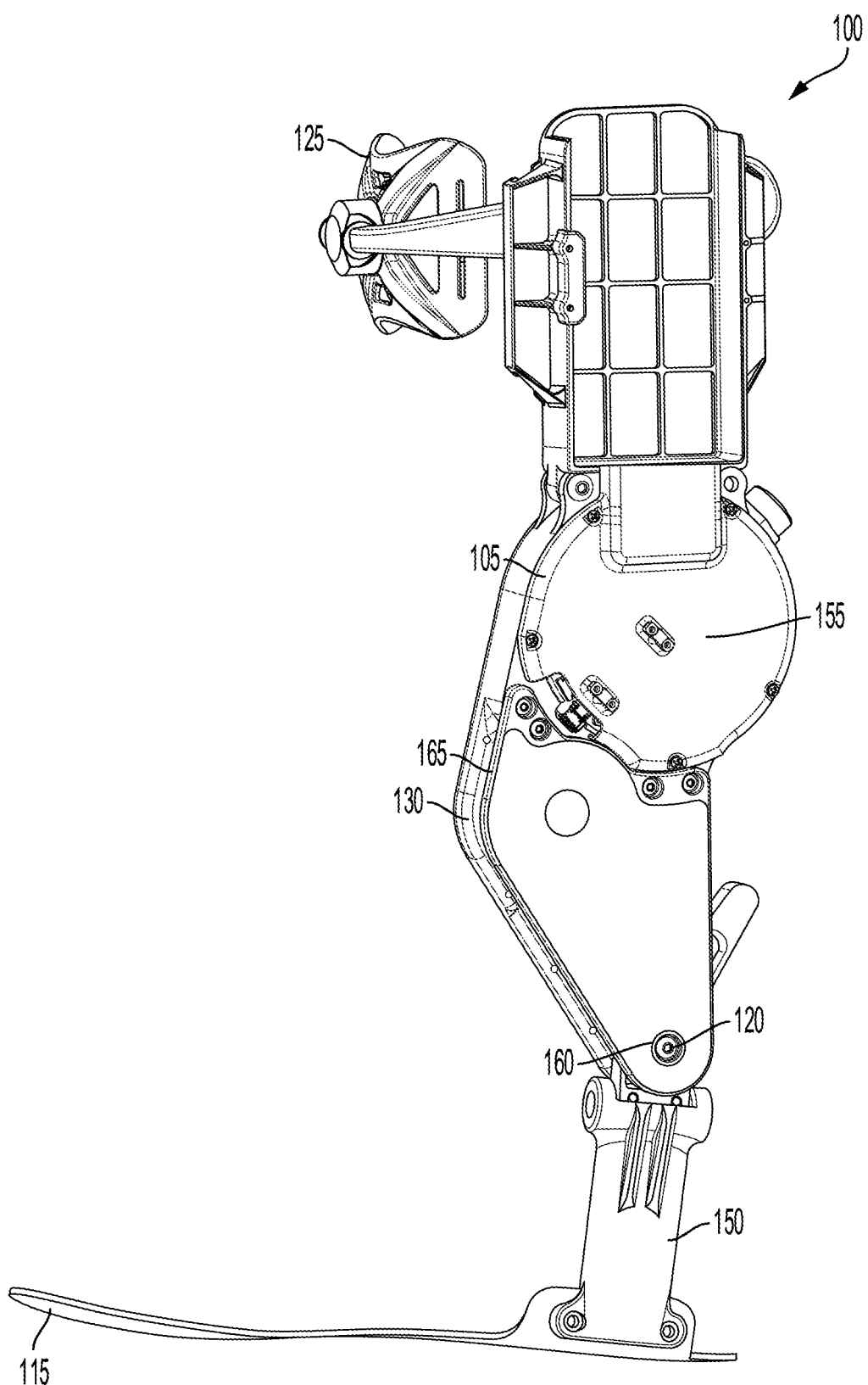
FIG. 7 illustrates a schematic diagram of an exoskeleton, according to an embodiment.

FIG. 7 illustrates a schematic diagram of the exoskeleton 100. The exoskeleton 100 can include the one or more housings 105, the footplate 115, the ankle joint component 120, the shin pad 125, the actuator 130, the post 150, the rotary encoder 155, the second rotary encoder 160, and the sealant 165 as described above. The one or more housings 105 can be coupled to the shin pad 125. The post 150 can couple the ankle joint component 120 with the footplate 115. The actuator 130 can include the one or more housings 105, the footplate 115, the ankle joint component 120, and the post 150. The rotary encoder 155 can measure an angle of the electric motor. The second rotary encoder 160 can measure an angle of the ankle joint.

Figure 8:
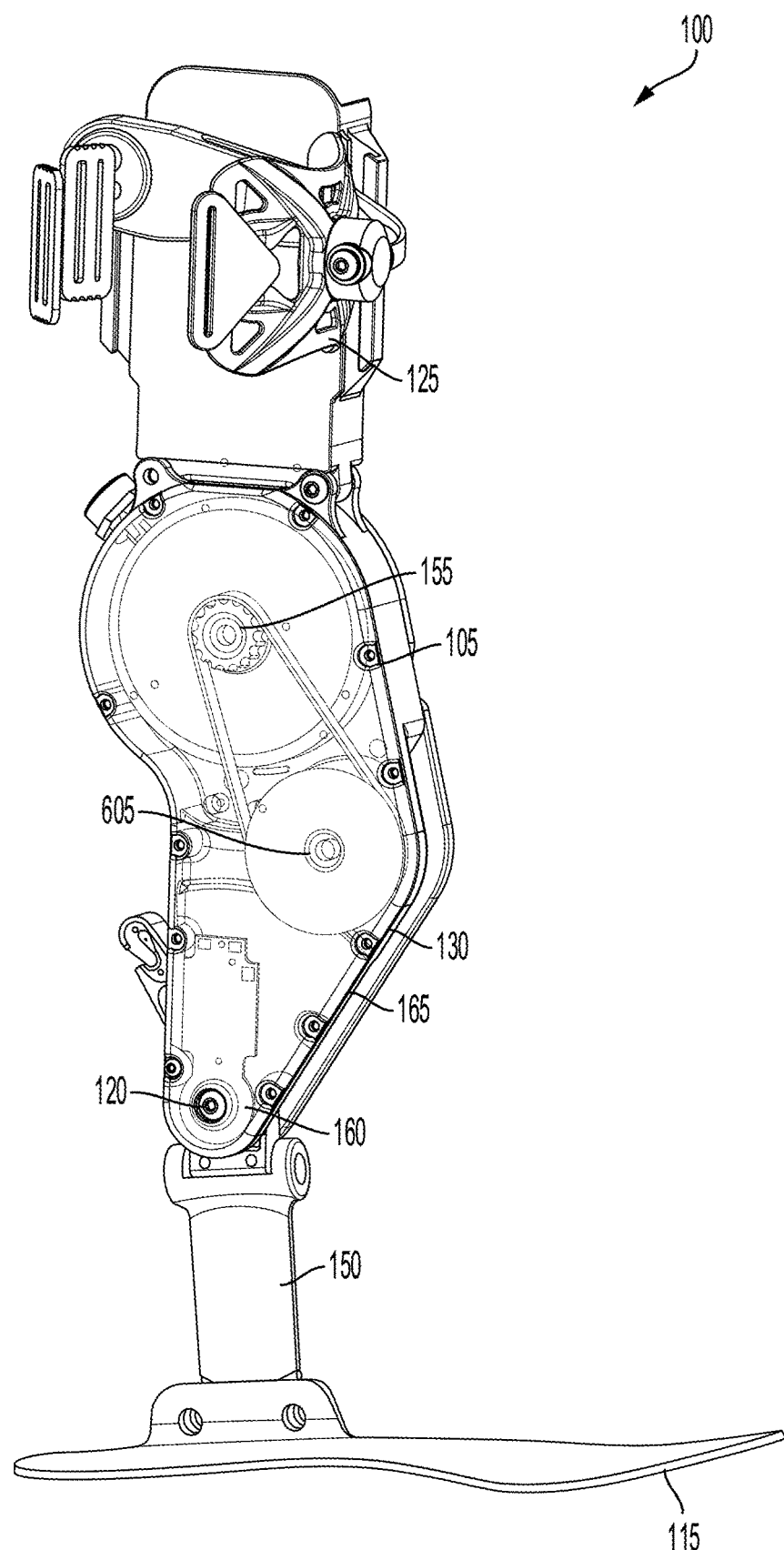
FIG. 8 illustrates a schematic diagram of an exoskeleton and internal parts, according to an embodiment.
Figure 9:
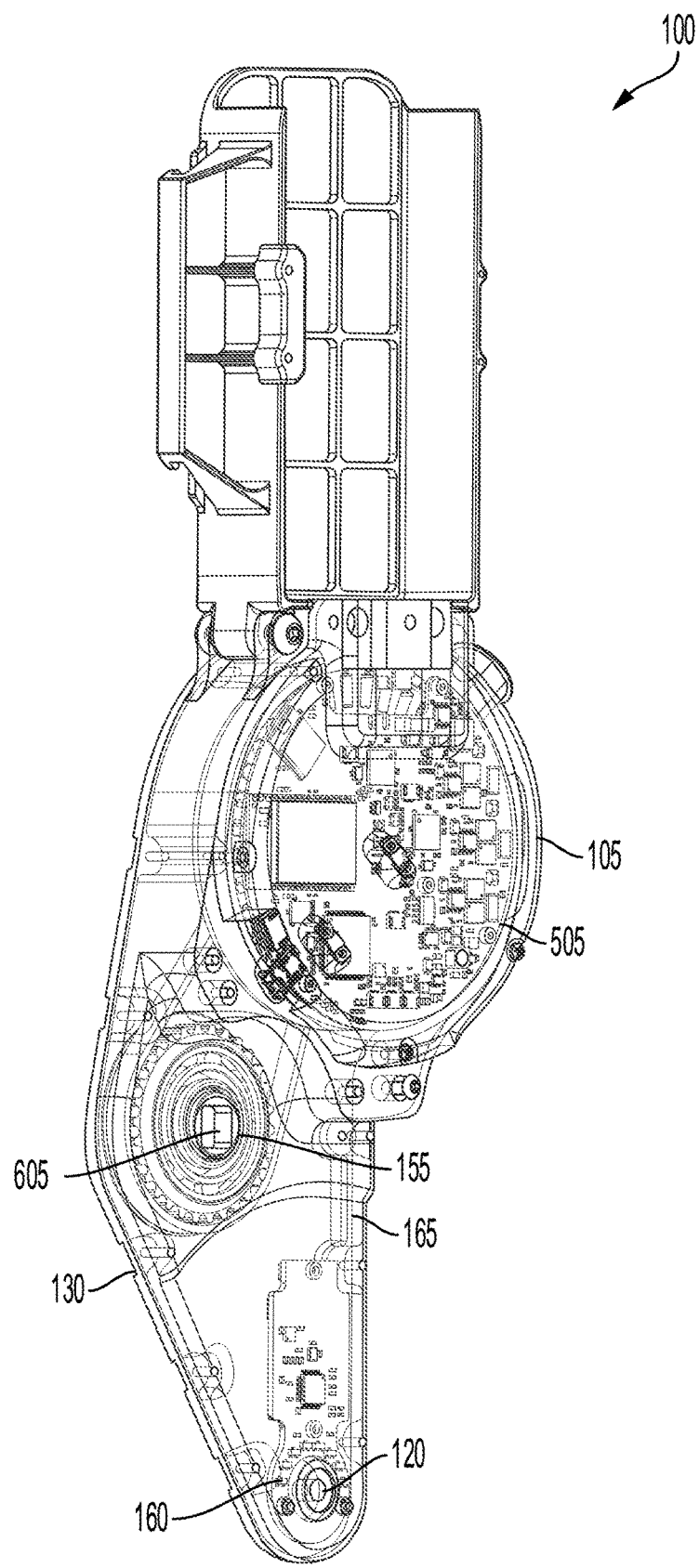
FIG. 9 illustrates a schematic diagram of an exoskeleton and internal parts, according to an embodiment.

FIG. 8 and FIG. 9 illustrate schematic diagrams of the exoskeleton 100 and internal parts. The exoskeleton 100 can include the one or more housings 105, the footplate 115, the ankle joint component 120, shin pad 125, the actuator 130, the post 150, the rotary encoder 155, the second rotary encoder 160, the sealant 165, and electronic circuitry 505 as described above. The internal parts can include an electronic circuit (e.g., circuitry). The electronic circuit can include individual electronic components (e.g., resistors, transistors, capacitors, inductors, diodes, processors, or controllers). The motor rotor can be connected to the output shaft 605.

Figure 10:
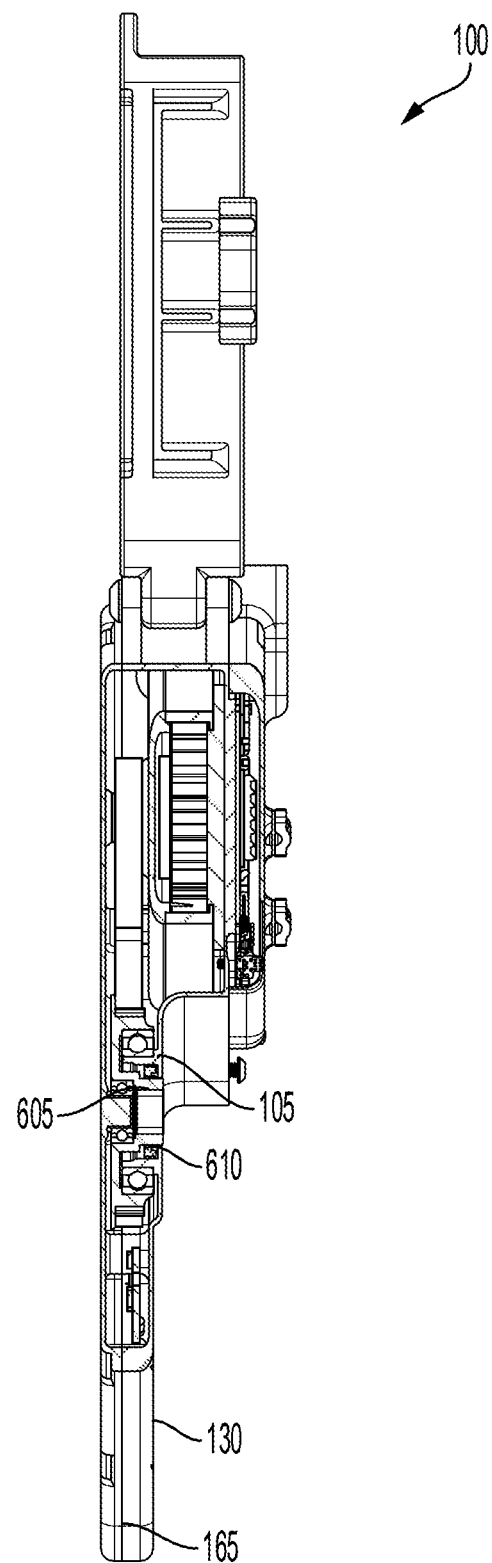
FIG. 10 illustrates a side view of an exoskeleton, according to an embodiment.

FIG. 10 illustrates a side view of the exoskeleton 100. The exoskeleton 100 can include the one or more housings 105, the actuator 130, the rotary encoder 155, the second rotary encoder 160, and the sealant 165, the output shaft 605, and the bore 610 as described above. The exoskeleton 100 can include an output shaft 605 (e.g., motor rotor). The output shaft 605 can be coupled to the electric motor. The output shaft 605 can extend through a bore 610 in a housing of the one or more housings 105 enclosing the electric motor. The bore 610 can receive the output shaft 605. A magnet can be located on a first side of the electric motor. An encoder chip can be located on the electronics board on the first side of the electric motor. The encoder chip can measure the angular position of the rotary encoder 155. An ankle shaft can extend through the second rotary encoder 160 which can increase the structural integrity of the exoskeleton 100. The exoskeleton 100 can include a transmission (e.g., gearbox) configured to couple the output shaft 605 to the electric motor. The transmission can include a machine in a power transmission system. The transmission can provide controlled application of power.

Figure 11:
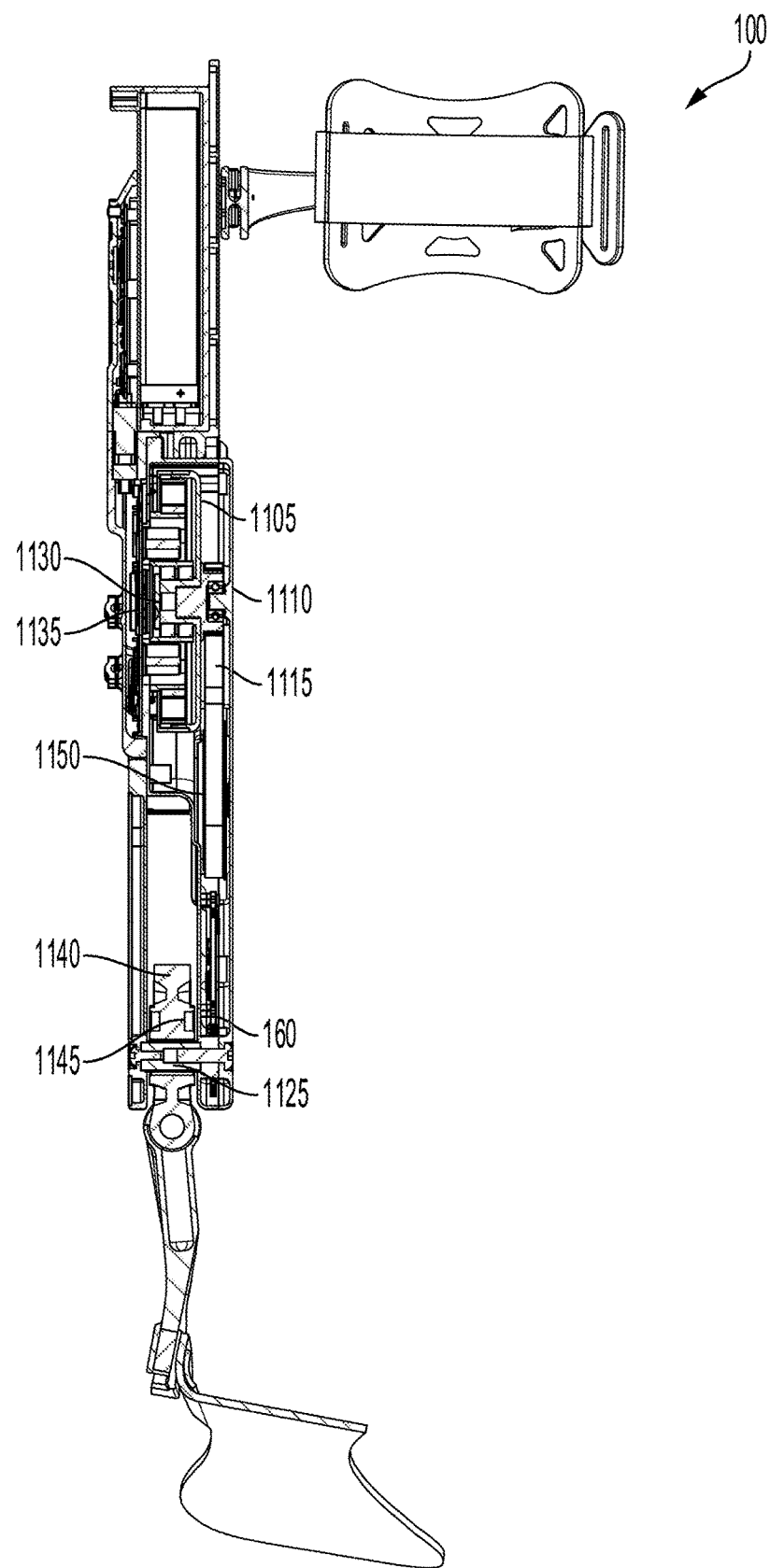
FIG. 11 illustrates a side view of an exoskeleton, according to an embodiment.

FIG. 11 illustrates a side view of an exoskeleton 100. The exoskeleton 100 can include a motor 1105 (e.g., electric motor), a motor timing pulley 1110 (e.g., timing pulley), a motor timing belt 1115 (e.g., timing belt), the second rotary encoder 160 (e.g., an ankle encoder PCB, ankle encoder printed circuit board, second rotary encoder PCB, or ankle encoder), an ankle shaft 1125, a motor encoder magnet 1130, a motor encoder 1135, a lever arm 1140 (e.g., ankle lever), and an ankle encoder magnet 1145. The ankle shaft 1125 can extend through the second rotary encoder 160 to increase the structural integrity of the exoskeleton 100. The motor timing belt 1115 can be coupled to a sprocket 1150. The sprocket 1150 can be coupled with a spool. The motor encoder magnet 1130 can be located on the first side of the electric motor.

Figure 12:
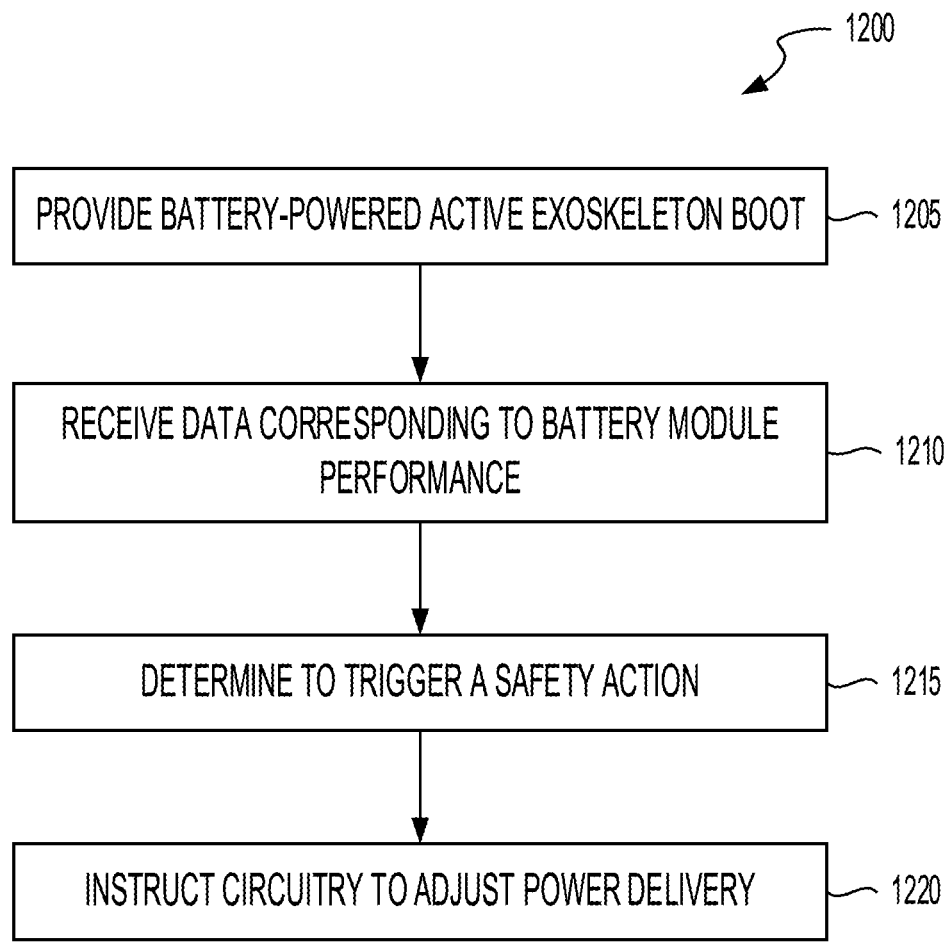
FIG. 12 illustrates a method of augmenting user motion, according to an embodiment.

FIG. 12 illustrates a method 1200 of augmenting user motion. The method 1200 can include providing, to a user, a battery-powered active exoskeleton boot (BLOCK 1205). The battery-powered active exoskeleton boot can include a shin pad to be coupled to a shin of a user below a knee of the user. The battery-powered active exoskeleton boot can include one or more housings enclosing electronic circuitry and an electric motor that can generate torque about an axis of rotation of an ankle joint of the user. At least one of the one or more housings can be coupled to the shin pad below the knee of the user. The battery-powered active exoskeleton boot can include a battery holder coupled to the shin pad. The battery holder can be located below the knee of the user and above the one or more housings enclosing the electronic circuitry. The battery-powered active exoskeleton boot can include a battery module removably affixed to the battery holder. The battery module can include a first power connector that electrically couples to a second power connector located in the battery holder while attached to the battery holder to provide electric power to the electronic circuitry and the electric motor. The battery-powered active exoskeleton boot can include an output shaft coupled to the electric motor and extending through a bore in a housing of the one or more housings enclosing the electric motor. The electronic circuitry can control delivery of power from the battery module to the electric motor to generate torque about the axis of rotation of the ankle joint of the user.

In some embodiments, the first power connector includes a blade connector. The second power connector can include a receptacle configured to receive the blade connector absent an exposed cable. The battery module can include a plurality of battery cells 305. The battery module can include a printed circuit board soldered to the plurality of battery cells 305. The battery module can include one or more battery balancers configured to actively transfer energy from a first battery cell 305 of the plurality of battery cells 305 to a second battery cell 305 of the plurality of battery cells 305 having less charge than the first battery cell 305. The battery module can include a signal trace, on the printed circuit board, that electrically connects the plurality of battery cells 305 to the one or more battery balancers.

In some embodiments, the method 1200 includes providing, via a serial data communication port of the first power connector, at least one of battery state data, a battery test function, a smart charging function, or a firmware upgrade. The battery state data can include the health of the battery module. The battery test function can include probing the battery module. The smart charging function can include using a high voltage to charge the battery module. A pin of the first power connector that provides serial data can be further configured to receive a voltage input greater than or equal to a threshold to wake up a battery management system of the battery module.

The method 1200 can include receiving data corresponding to battery module performance (BLOCK 1210). For example, the method 1200 can include receiving, by one or more processors of the battery-powered active exoskeleton boot, data corresponding to a performance of the battery module, the data comprising one or more of a temperature, current, voltage, battery percentage. For example, the data can include a temperature from one or more temperature sensors of the computing system. The data can include a temperature from one or more temperature sensors of the battery module.

The method 1200 can include determining to trigger a safety action (BLOCK 1215). For example, the method 1200 can include determining, by the one or more processors, based on a safety policy, to trigger a safety action. The safety policy can include triggering the safety action if a threshold temperature, voltage or battery percentage is crossed. For example, the safety policy can include triggering the safety action if a temperature of one or more of the plurality of battery cells 305 is higher than a threshold temperature. The safety policy can include triggering the safety action if a battery percentage of the battery module is below a threshold battery percentage. The measured temperature can include the temperature of the printed circuit board and battery cells 305. The measured temperature can include the temperature of the printed circuit board and battery cells 305 measured in two locations. The safety policy can include triggering the safety action if a measured voltage is higher than the threshold voltage.

The method 1200 can include instructing circuitry to adjust power delivery (BLOCK 1220). For example, the method 1200 can include instructing, by the one or more processors, based on the safety action, the electronic circuitry to adjust delivery of power from the battery module to the electric motor to reduce an amount of torque generated about the axis of rotation of the ankle joint of the user. The safety action can include lowering or reducing the amount of torque generated about the axis of rotation of the ankle joint of the user. The safety action can include increasing the amount of torque generated about the axis of rotation of the ankle joint of the user.

Figure 13:
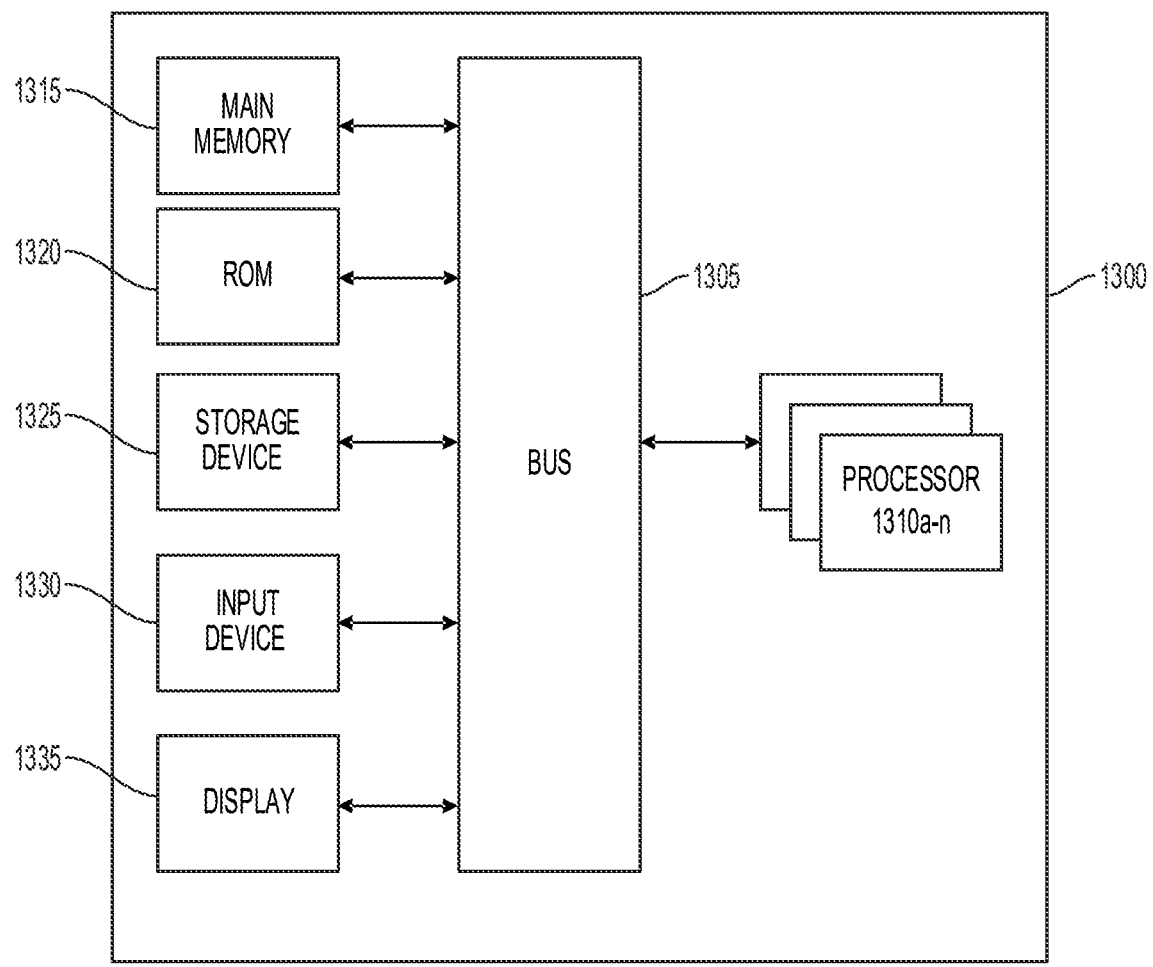
FIG. 13 illustrates a block diagram of an architecture for a computing system employed to implement various elements of the system and methods depicted in FIGS. 1-16, according to an embodiment.

FIG. 13 illustrates a block diagram of an architecture for a computing system employed to implement various elements of the system and methods depicted in FIGS. 1-16, according to an embodiment. FIG. 13 is a block diagram of a data processing system including a computer system 1300 in accordance with an embodiment. The computer system can include or execute a coherency filter component. The data processing system, computer system or computing device 1300 can be used to implement one or more components configured to process data or signals depicted in FIGS. 1-12 and 14-16. The computing system 1300 includes a bus 1305 or other communication component for communicating information and a processor 1310*a-n* or processing circuit coupled to the bus 1305 for processing information. The computing system 1300 can also include one or more processors 1310 or processing circuits coupled to the bus for processing information. The computing system 1300 also includes main memory 1315, such as a random access memory (RAM) or other dynamic storage device, coupled to the bus 1305 for storing information, and instructions to be executed by the processor 1310. Main memory 1315 can also be used for storing time gating function data, temporal windows, images, reports, executable code, temporary variables, or other intermediate information during execution of instructions by the processor 1310. The computing system 1300 may further include a read only memory (ROM) 1320 or other static storage device coupled to the bus 1305 for storing static information and instructions for the processor 1310. A storage device 1325, such as a solid state device, magnetic disk or optical disk, is coupled to the bus 1305 for persistently storing information and instructions.

The computing system 1300 may be coupled via the bus 1305 to a display 1335 or display device, such as a liquid crystal display, or active matrix display, for displaying information to a user. An input device 1330, such as a keyboard including alphanumeric and other keys, may be coupled to the bus 1305 for communicating information and command selections to the processor 1310. The input device 1330 can include a touch screen display 1335. The input device 1330 can also include a cursor control, such as a mouse, a trackball, or cursor direction keys, for communicating direction information and command selections to the processor 1310 and for controlling cursor movement on the display 1335.

The processes, systems and methods described herein can be implemented by the computing system 1300 in response to the processor 1310 executing an arrangement of instructions contained in main memory 1315. Such instructions can be read into main memory 1315 from another computer-readable medium, such as the storage device 1325. Execution of the arrangement of instructions contained in main memory 1315 causes the computing system 1300 to perform the illustrative processes described herein. One or more processors in a multi-processing arrangement may also be employed to execute the instructions contained in main memory 1315. In some embodiments, hard-wired circuitry may be used in place of or in combination with software instructions to effect illustrative implementations. Thus, embodiments are not limited to any specific combination of hardware circuitry and software.

Although an example computing system has been described in FIG. 13, embodiments of the subject matter and the functional operations described in this specification can be implemented in other types of digital electronic circuitry, or in computer software, firmware, or hardware, including the structures disclosed in this specification and their structural equivalents, or in combinations of one or more of them.

III. Bilateral Wireless Communication

Systems, methods and devices of the present technical solution are directed to control strategies for bilateral wireless communication between multiple exoskeleton devices. An exoskeleton device can provide human augmentation to a user during different movements and activities (e.g., walking running, jumping) to reduce a physiological impact on the user during the movement. For example, the exoskeleton devices can include exoskeleton boots worn by a user that provide force, power and/or torque to a limb (e.g., leg, ankle, knee) and joints of the user during different movements. The force, power and/or torque to the limb can reduce the amount of force or effort needed by the user to perform the movement to, for example, enhance a performance of the user during the movement and/or reduce an amount of energy expended by the user to perform the movement.

The exoskeleton devices can include and/or connect to a plurality of sensors (e.g., inertial measurement unit, joint angle sensors, torque sensors) to receive measurements during different activities of the user and calculate appropriate force and/or torque to provide to the user during an activity or movement. The exoskeleton devices can communicate the sensor data to make informed force and torque determinations and improve control capability of the exoskeleton system worn by the user. For example, one exoskeleton device may sense an activity transition before the other exoskeleton device(s) and can inform the other exoskeleton device and/or entire exoskeleton system worn by the user. The multiple communicatively connected exoskeleton devices can provide increased control strategies that use or rely on data from the other respective exoskeleton devices. The exoskeleton devices can be worn on separate joints (e.g., right leg, left leg) and communicate, for example, through a wireless connection to eliminate the use of wires crossing different joints of the body of the user. The wireless connection can reduce sang hazards and make it easier for a user to take on and off the exoskeleton devices. The bilateral communication between the exoskeleton devices through wireless connections can enhance a performance of the user during dynamic activities such as running, and for activities requiring leg synchronization such as squatting then jumping.

However, the communication between the multiple exoskeleton devices can experience issues, delays or a connection can be lost. For example, wireless communication can be intrinsically susceptible to interference as compared to wired communication. The interference can reduce the quality of the bilateral link between different exoskeleton devices, resulting in errors or delays. The interference between communication systems of the respective exoskeleton devices (e.g., bilateral radios, Bluetooth device) can corrupt data or prevent a connection between different exoskeleton devices. In some embodiments, the interference can be between exoskeleton devices worn by two different users resulting in issues in communication between the respective two users. The wireless connection between multiple exoskeleton devices can experience latency resulting in delayed or lost sensor data. This latency delay can cause issues as, depending on the particular movement, the exoskeleton devices may use the data rapidly to generate appropriate force and/or torque to the user during a running event or jumping event. If the data is delayed or received after a particular time threshold, the data can be less accurate and/or less relevant. Power devices may use a battery pack worn around a waist of the user that powers each device worn by the respective user and thus, not use a wireless connection between devices. Medical devices can include a single device worn to address only a particular pathology or injury and thus, not use multiple devices and communications between different devices.

The systems and methods described herein can include multi-control strategies that use real-time latency measurements to determine a control strategy and reduce the need for communication between the exoskeleton devices to be available and reduce performance issues when communication between the exoskeleton devices is unavailable. The exoskeleton devices worn by a user or multiple users can measure and determine a latency in communication between the respective devices and select a state (e.g., control state, operation state) based in part on the latency to determine whether to accept or reject data from the other device.

The exoskeleton devices can include a controller (e.g., processor) that transmits, processes and receives packets including sensor data. The controller can transmit a packet, initiate a timer and wait for a response from another exoskeleton device. Upon receiving the response or a second packet, the controller can end the timer and determine a latency for communications between the two devices based in part on the measured time value. The exoskeleton device can include multiple states and select a state based in part on the determined latency. For example, the latency can be compared to a time threshold and if the latency is less than the time threshold, the controller can determine data from the other exoskeleton device to be valid and accept the data as the data is received within the time threshold (e.g., low latency). The controller can select the first state for the exoskeleton device to accept the data and, for example, use the data to determine force and/or torque values for a current movement and/or one or more subsequent movements. If the latency is greater than the time threshold, the controller can determine data from the other exoskeleton device to be invalid (e.g., no longer relevant) and reject the data as the data is received outside the time threshold (e.g., high latency). The controller can select the second state for the exoskeleton device to reject the data and, instead, use previous data and data from the exoskeleton device the controller is a component of to determine force and/or torque values for a current movement and/or one or more subsequent movements. The controller can use the latency measurement to select a control strategy for the exoskeleton device to reduce or eliminate issues associated with a wireless connection and increase a performance of the user wearing the exoskeleton device.

In embodiments, the controller can use the latency measurement to assign weight values indicating an importance of different sensor data, for example, to weigh newer or more recent data greater than older data. The controller can determine or identify missed or corrupted packets during communications between exoskeleton devices and determine an appropriate state for the exoskeleton device based in part on a time value since a last valid packet was received from the other exoskeleton device. An allowable time since a last valid packet from a partner device can be dependent on the respective exoskeleton device and/or a controller state of the exoskeleton device.

The exoskeleton device can execute real-time techniques to measure and determine communication latency. For example, a first exoskeleton device can transmit a labeled packet and time how long it takes to receive a response or next correctly labeled packet from a partner device. If the time (e.g., response time) is within a determined range or under a threshold, the controller of the exoskeleton device can determine the packet is valid and data included with the packet is valid. In some embodiments, the exoskeleton devices can communicate in a master/slave configuration with a first exoskeleton device identified as a master device and one or more second exoskeleton devices identified as slave devices. The controller can determine packets to be invalid if the time value associated with the packet is outside an acceptable range, greater than a threshold, greater than a nominal value, or if the packet is different than what the controller expected to receive.

The exoskeleton devices described herein can account for the communication latency between partner devices and modify control parameter determinations based in part on the communication latency. A controller of an exoskeleton device can use data received via wireless communication "as-is" or the controller can extrapolate the data based on a latency measurement and derivatives of the data. For example, if a first exoskeleton receives an ankle angle measurement of X degrees, an ankle velocity of Y degrees per millisecond (ms), and determine a latency of Z ms, the controller of the first exoskeleton can use the calculated ankle value of $X+(Y*Z)$. Thus, the systems and methods described herein can determine a communication latency between partner devices to determine the control strategy for the respective exoskeleton device and maintain or increase a performance of the user wearing the respective exoskeleton device during different movements or activities, for example, independent of the status of the communication connection between the partner devices.

Figure 14:
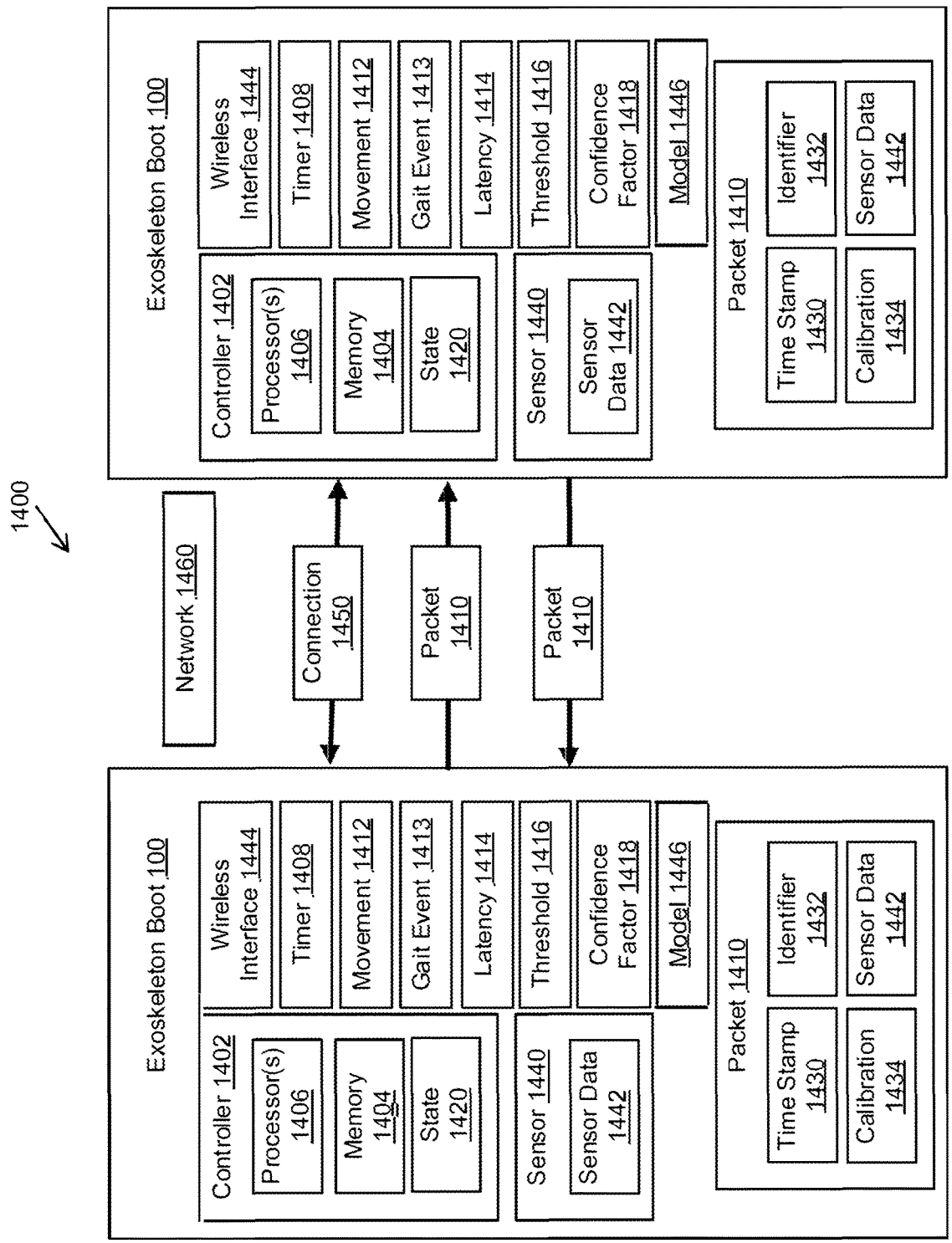
FIG. 14 is a block diagram of a system for bilateral wireless communication between multiple exoskeleton devices in accordance with an illustrative embodiment.

Referring to FIG. 14, depicted is a block diagram of one embodiment of a system 1400 having a first exoskeleton boot 100 and a second exoskeleton boot 100. The exoskeleton boots 100 worn by a user or multiple users can measure and determine a latency communication between the respective exoskeleton boots 100 and select a state (e.g., control state, operation state) based in part on the latency to determine whether to accept or reject data from the other exoskeleton boot 100. The exoskeleton boots 100 can execute multi-control strategies that use real-time latency measurements to determine a control strategy and reduce the need for communication between the exoskeleton boots 100 to be available and reduce performance issues when communication between the exoskeleton boots 100 is unavailable.

The exoskeleton boots 100 can be a user on one or both lower limbs (e.g., right leg, left leg) to aid the user in performing movements and/or activities (e.g., walking, running, hiking). The exoskeleton boots 100 can provide force or torque to the respective limb to reduce an amount of force provided by the user to perform the movement and reduce a physiological impact on the user during the movement. The exoskeleton boots 100 can communicate during the movements performed by the user to provide user feedback and modify control parameters of the exoskeleton boots 100. For example, the exoskeleton boots 100 can include or connect to a plurality of sensors 1440 that monitor and record sensor data 1442 (e.g., measurements, gait state, joint angles, speed, body positioning) of the user during the movement. The measurements or sensor data 1442 can be used to calculate force or torque provided by an exoskeleton boot 100 at a particular time such as during the movement and/or for one or more subsequent movements. The exoskeleton boots 100 can communicate to share the sensor data 1442 to provide increased control capability of the exoskeleton boots 100 and an increased performance of the user during the movement. The exoskeleton boot 100 can be the same as or substantially similar to exoskeleton 100 described herein with respect to FIG. 1 or any type of exoskeleton described herein.

It should be appreciated that although FIG. 14 displays two exoskeleton boots 100, the multi-control and communication techniques described herein can include any number of exoskeleton devices (e.g., exoskeleton boots, exoskeleton). For example, the multi-control and communication techniques described herein can be applied to a group of users (e.g., military unit having two or more members, adventure group having two or more members) such that the exoskeleton boots 100 worn by each user can communicate with one or more or all of the exoskeleton devices worn by any of the other users in the respective group. Thus, multi-control and communication techniques described herein can be scaled accordingly for single user operations and multi-user operations.

The exoskeleton boot 100 an include a controller 1402. The controller 1402 can be implemented using hardware or a combination of software and hardware. For example, each component of the controller 1402 can include logical circuitry (e.g., a central processing unit or CPU) that responses to and processes instructions fetched from a memory unit (e.g., memory 1404). Each component of the controller 1402 can include or use a microprocessor or a multi-core processor. A multi-core processor can include two or more processing units (e.g., processor 1406) on a single computing component. Each component of the controller 1402 can be based on any of these processors, or any other processor capable of operating as described herein. Each processor can utilize instruction level parallelism, thread level parallelism, different levels of cache, etc. For example, the controller 1402 can include at least one logic device such as a computing device having at least one processor 1406 to communicate, for example, with one or more exoskeleton boots 100 and/or one or more other controllers 1402 of one or more other exoskeleton boots 100. The components and elements of the controller 1402 can be separate components or a single component. The controller 1402 can include a memory component (e.g., memory 1404) to store and retrieve sensor data 1442. The memory 1404 can include a random access memory (RAM) or other dynamic storage device, for storing information, and instructions to be executed by the controller 1402. The memory 1404 can include at least one read only memory (ROM) or other static storage device for storing static information and instructions for the controller 1402. The memory 1404 can include a solid state device, magnetic disk or optical disk, to persistently store information and instructions. The controller 1402 can be the same as or substantially similar to any controller or microcontroller described herein.

The controller 1402 can execute or perform multi-control strategies that use real-time latency measurements to determine a control strategy and reduce the need for communication between the exoskeleton boots 100 to be available and reduce performance issues when communication between the exoskeleton boots 100 is unavailable. For example, the controller 1402 can transition an exoskeleton boot 100 from a first state 1420 to a second, different state 1420 based in part on a latency 1414 between the exoskeleton boot 100 and at least one other different exoskeleton boot 100.

The latency 1414 can include or correspond to a time value for an exoskeleton boot 100 to transmit a packet 1410 and receive a response (e.g., second packet 1410) from at least one other exoskeleton boot 100 or a time delay indicating how long it takes the exoskeleton boot 100 to receive a next or subsequent correctly labeled packet 1410 (e.g., response to a transmitted packet 1410). The latency 1414 can include or correspond to a time interval, time delay or time difference between the transmission of at least one packet 1410 by an exoskeleton boot 100 and receipt of a response to the at least one packet 1410 or a receipt of a subsequent packet 1410 at the respective exoskeleton boot 100.

The exoskeleton boot 100 can couple with or connect to (e.g., wireless connection) to a display 1335 (e.g., display device). The display 1335 can provide, for example, information to a user of the exoskeleton boot 100 including but not limited to, torque values, forces values, performance indicators, historical data and/or data associated with the user performing one or more movements 1412 wearing the exoskeleton boot 100. The display 1335 can provide or display one or more visual indications. A visual indication can include a video of a user performing a movement 1412, an image of the user performing a movement 1412, a marker, menu, window or selectable content item provided through the display 1335. The visual indication can include a menu or listing of torque values available for selection through the display 1335 or user interface 1330 portion of the display 1335 (e.g., touch screen, selectable content items).

In embodiments, a user interface 1330 (e.g., input device) can couple with or connect to the display 1335 to, for example, enable a user to interact with content provided through the display 1335 and provide feedback to the controller 1402. The user interface 1330 can include enable interaction with one or more visual indications provided through the display 1335 and responsive to an interaction (e.g., select, click-on, touch, hover), the user interface 1330 can generate an indication identifying a user input and/or selection of at least one content item (e.g., visual indication). The user interface 1330 can couple to or connect with the controller 1402 and/or exoskeleton boot 100 to provide the indication. In some embodiments, the display 1335 can receive the indication from the user interface 1330 and transmit or provide the indication to the controller 1402 and/or exoskeleton boot 100.

A state 1420 can control or indicate whether an exoskeleton boot 100 trusts or accepts data and packets 1410 from a partner device (e.g., second exoskeleton boot 100) or does not accept and/or discards data or packets 1410 from a partner device (e.g., second exoskeleton boot 100). The controller 1402 can use the determined or measured latency 1414 between the exoskeleton boots 100 to select a state 1420 for an exoskeleton boot 100. For example, if the latency 1414 is less than or below a threshold 1416, the controller 1402 or exoskeleton boot 100 can select or implement a first state 120 indicating that packets 1410 from the partner exoskeleton boot 100 are valid and sensor data 1442 received with the one or more packets 1410 are valid. In embodiments, in a first state 1420, the exoskeleton boot 100 can accept one or more packets 1410 from one or more other exoskeleton boots 100 and sensor data 1442 received with the one or more packets 1410, for example, to use the sensor data 1442 to perform one or more movements 1412. In embodiments, if the latency 1414 is greater than a threshold 1416, the controller 1402 or exoskeleton boot 100 can select or implement a second state 1420 indicating that packets 1410 from the partner exoskeleton boot 100 are not valid (e.g., old data, not current reliable data) and sensor data 1442 received with the one or more packets 1410 is to be rejected. In the second state 1420, the exoskeleton boot 100 may reject, ignore or not use packets 1410 and sensor data 1442 from a partner exoskeleton boot 100 to perform one or more movements 1412, and instead, use sensor data 1442 obtained by itself or sensor data 1442 previously received from one or more partner exoskeleton boots 100.

A packet 1410 can include data, a data structure, a data unit, or a collection of data (e.g., contiguous data units). The packet 1410 can include one or more portions, including but not limited to, a header portion and/or a payload portion, including information associated with the packet 1410 and/ or a device transmitting the packet 1410 or to receive the packet 1410 (e.g., intended target device). For example, a packet 1410 can include or identify a source device and a destination device and include content (e.g., sensor data 1442, calibration data 1434) being transferred. The packet 1410 can include a time stamp 1430, an identifier 1432, sensor data 1442 and/or calibration data 1434, for example, to calibrate communications between at least two exoskeleton boots 100. The time stamp 1430 can indicate or identify a time the respective packet 1410 was transmitted. The identifier 1432 can indicate or identify the respective exoskeleton boot 100 that generated and transmitted the packet 1410. The calibration data 1434 can include information (e.g., bandwidth, data rate, type) on a connection 1450 between two or more exoskeleton boots 100 and/or a pairing signal used to calibrate the connection 1450 between the two or more exoskeleton boots 100.

The sensor data 1442 can include, but is not limited to, motion data, force data, torque data, temperature data, speed, gait transitions (e.g., gait event), angle measurements (e.g., of different joints of the user, joint angle measurements), state information, and/or movement information. The sensor data 1442 can include data corresponding to steady state activities or transient activities. The sensor data 1442 can include any form of data associated with, corresponding to or generated in response one or more movements 1412 and/or activities performed or executed by the user wearing one or more exoskeleton boots 100. For example, the sensor data 1442 can include data associated with a movement 1412 or motion performed or executed by the user and/or any type of use of one or more muscles of the user, for example, that may not involve motion (e.g., holding a position, standing) while wearing the exoskeleton boot 100. The sensor data 1442 can include ankle joint data, inertial measurement unit data, and/or battery data.

In embodiments, the sensor data 1442 can include inertial measurement unit (IMU) data, goniometer data, infrared reflector data, force plate data, electromyography (EMG) data, and heartrate data. In embodiments, the sensor data 1442 can include data corresponding to motor values, voltage values, current, temperature, positional, state information, walking, running, gait state, stance, stance begin and end, swing, swing begin and end, peak plantarflexion, peak dorsiflexion, heel strike, toe off, body segment positions, orientations, velocity, acceleration, energy, power, power levels, battery, capacity, safety, warnings, and/or errors.

In embodiments, the sensor data 1442 can include historical data, historical sensor data, historical video data and historical motion capture data. The historical sensor data 1442 can include previous sensor data 1442 associated with the user performing one or more movements 1412 or sensor data 1442 from one or more other, different users performing one or more movements 1412. The historical video data can include one or more videos, images or stream of images of the user and/or one or more other, different users performing one or more movements 1412. The historical motion capture data can include one or more recordings or images of the user and/or one or more other, different users performing one or more movements 1412.

The sensor data 1442 can include or correspond to data collected via the exoskeleton boot 100 in a plurality of modes, for example, an unpowered mode, a partially powered mode, and a fully powered mode. The controller 1402 can perform one or more of the following, averaging, filtering, aggregating and/or merging to process the sensor data 1442 and generate or provide the model 1446. For example, the controller 1402 can average the sensor data 1442 to identify patterns, trends or similarities across different data points. The controller 1402 can filter the sensor data 1442 to identify patterns, trends or similarities across different data points. The controller 1402 can aggregate or merge the sensor data 1442 to identify patterns, trends or similarities across different data points. In embodiments, the controller 1402 can generate a data set using the sensor data 1442 to provide to the model 1446, for example, for training the model 1446.

The sensors 1440 can include a variety of different sensors to detect or measure, such as but is not limited to, device properties, gait state, joint angles, speed, and/or body positioning information. In embodiments, the sensors 1440 can include, but are not limited to, IMU sensors, joint angle sensors, motor sensors, voltage sensors, current sensors, temperature sensors, angle sensors, positional sensors, torque sensors, force sensors, velocity, accelerations, energy sensors, power sensors, and/or battery sensors. The sensors 1440 can include inertial measurement unit (IMU) sensors, goniometer, infrared reflectors, force plates, electromyography (EMG), and/or heartrate monitors or sensors.

The threshold 1416 can include a value, range of values, or a percentage. The threshold 1416 can indicate a limit or magnitude that if exceeded or less than, a transition in a state 1420 may occur for at least one exoskeleton boot 100. In embodiments, the threshold 1416 can include a time value, time period or time range to form a time threshold. The threshold 1416 can indicate a time threshold 1416 to measure latency 1414 between two or more exoskeleton boots 100. In some embodiments, if the latency 1414 is less than the time threshold 1416, the controller 1402 can determine packets 1410 and data from the other exoskeleton boot 100 to be valid and accept the packet 1410 and associated data as the packet 1410 and associated data is received within the time threshold 1416 (e.g., low latency). In some embodiments, if the latency 1414 is greater than the time threshold 1416, the controller 1402 can determine packet 1410 and associated data from the other exoskeleton boot 100 is invalid (e.g., no longer relevant) and reject the packet 1410 and associated data as the packet 1410 and associated data is received outside the time threshold 1416 (e.g., high latency). The number or value of the threshold 1416 can vary based at least in part on properties of a connection 1450 between different exoskeleton boots 100 and/or properties of the respective exoskeleton boots 100.

The movement 1412 can include any type of motion performed or executed by user and/or any type of use of one or more muscles of the user, for example, that may not involve motion (e.g., holding a position, standing). The movement 1412 can include can include, but is not limited to, physical activity, walking, running, standing, standing up, ascend or descend a surface (e.g., stairs), jogging, springing, jumping (e.g., single leg or both legs) squat, crouch, kneel or kick. In embodiments, the movement 1412 can include, but is not limited to, walking, running, gait state, gait transition (e.g., walking to running), stance begin and end, swing, swing begin and end, peak plantarflexion, peak dorsiflexion, heel strike, and/or toe off.

The controller 1402 can store and maintain data, including sensor data 1442 received from one or more sensors 1440 connected to the exoskeleton boot 100 and/or sensor data 1442 received in one or more packets 1410 from one or more other exoskeleton boots 100, based in part on time intervals corresponding to a time period when one or more movements 1412 were performed. Time intervals can include or correspond to a time period or range of time having an initial time and an end time. The number of time intervals can vary (e.g., first time interval, second time interval) and be based at least in part on a number of movements 1412 tracked, a number of users, and/or an amount of sensor data 1442.

The controller 1402 and/or exoskeleton boot 100 can determine a confidence factor 1418 for a packet 1410 and data (e.g., sensor data 1442, calibration data 1434) received with the respective packet 1410. The confidence factor 1418 can include a confidence level, confidence score, and/or confidence threshold for the packet 1410 and be based in part on the time value or latency 1414 associated with the packet 1410. In embodiments, the confidence factor 1418 can indicate a trust level or confidence in data (e.g., sensor data 1442, calibration data 1434) received with the packet 1410. The confidence factor 1418 can include a weighting value applied to the data from the packet 1410 to increase a weight or importance of more recent or newer data and decrease a weight or importance of older data. For example, a long delay or higher latency 1414 between communications between different partner devices (e.g., between exoskeleton boots 100) can indicate an issue with at least one of the partner devices and can result in a lower assigned confidence factor 1418. A short delay or low latency 1414 between communications between different partner devices (e.g., between exoskeleton boots 100) can indicate a strong connection between the partner devices, that the devices are functioning properly and can result in a greater or increased confidence factor 1418.

The exoskeleton boot 100 can include a model 1446 (e.g., command modelling system). The model 1446 can generate commands or control parameters to instruct the exoskeleton boot 100 on a level of torque or force to provide to perform a movement 1412. The model 1446 can be implemented using hardware or a combination of software and hardware. The model 1446 can include logical circuitry (e.g., a central processing unit or CPU) that responses to and processes instructions fetched from memory 1404. The model 1446 can include a processor and/or communicate with processor 1406 to receive instructions and execute instructions received, for example, from controller 1402.

In embodiments, the model 1446 can include or execute a machine learning device (e.g., machine learning engine) having one or more machine learning algorithms and/or an artificial intelligence (AI) device. The model 1446 can include a machine learning model (e.g., artificial intelligence model) trained using training data, sensor data 1442 and/or data included in one or more packets 1410. For example, the sensor data 1442 connected to an exoskeleton boot and data (e.g., sensor data 1442) from one or more packets 1410 from other exoskeleton boots 100 can be provided as input to the machine learning model, which can be caused to generate data or control parameters for performing one or more movements 1412. The model 1446 can be updated in real-time, for example, as additional sensor data 1442 and data from one or more packets 1410 is received and accepted. In embodiments, the model 1446 can be trained to predict torque values and generate one or more commands corresponding to the torque values. The model 1446 can identify patterns or similarities between different data points of the received input (e.g., sensor data 1442) and map the inputs to outputs that correspond to the identified patterns (e.g., ankle angle data, torque used to transition between walking and running in previous activities). The model 1446 can generate the commands to control operation of the exoskeleton boot 100 based in part on the identified patterns in the received input data (e.g., sensor data 1442, data from packets 1410).

The commands can include an instruction, task or function generated by the model 1446 and provided to an exoskeleton boot 100 to instruct the exoskeleton boot 100 a level or amount of torque, force, velocity or a combination of torque, force and velocity (e.g., impedance) to generate to aid a user wearing the respective exoskeleton boot 100 in performing a movement 1412. In embodiments, the commands can include a data structure indicating a desired, requested or target torque, force and/or velocity level. The commands can include or correspond to a torque profile that includes one or more torque values (e.g., or force values, velocity values) for the exoskeleton boot 100 to apply to a lower limb of a user to augment or aid the user in performing a movement 1412.

The model 1446 can include a machine learning device to execute one or more machine learning algorithms and/or artificial intelligence (AI) engines to turn the received inputs (e.g., sensor data 1442) into a model and one or more predictions for generating commands. The inputs can include but is not limited to, sensor data 1442, historical data, indications and one or more torque values. The inputs can include sensor data 1442 associated with a plurality of users of varying ages, sizes and ability levels or users in a similar age range, size range and/ability range as a current user of the exoskeleton boot 100. The inputs can include sensor data 1442 associated with a plurality of different types of activities, states (e.g., transient state, steady state) and/or power levels (e.g., unpowered, low power level, full power level) to learn and train the model 1446 across a variety of different movement patterns. The controller 1402 can receive sensor data 1442 from one or more users to provide a larger data set to train the model 1446. For example, the controller 1402 can provide sensor data 1442 from different users to provide a variety of different data points that include information on various conditions (e.g., environmental) and different type of users and generate an increased level of training data to train the model 1446 initially prior a respective user generating a determined amount of sensor data 1442 on their own.

In some embodiments, the controller 1402 can continually and/or in real-time provide one or more of the sensor data 1442. historical data, indications and one or more torque values to execute and train the model 1446, for example, during a series of movements 1412 to update the model 1446 and generate new subsequent commands as a user transitions between the different movements 1412 in a series of movements 1412. In embodiments, the users can wear the exoskeleton boots 100 and the controller 1402, through the model 1446, can provide real-time optimization to alter commands or generate new commands to reach a desired torque value or output by the exoskeleton boot 100 to augment of movement 1412 performed by the user. In some embodiments, the user can provide real-time feedback to the controller 1402 and model 1446, for example, through selection of a torque value (e.g., indication) via a user interface 1330 and alter the users own respective torque value in real-time.

The model 1446 can process the received inputs using a machine learning device to apply one or more machine learning algorithms and/or AI techniques to the received inputs and generate commands for instructing and controlling the exoskeleton boot 100. For example, the model 1446 can be trained to predict torque values and torque profiles and generate one or more commands corresponding to the torque values and torque profiles. The model 1446 through the machine learning device can identify patterns or similarities between different data points of the received input. The controller 1402 can train the model 1446 to predict how the application of a particular level of torque, force and/or velocity can impact the movement, gait and/or performance of a user performing one or more movements 1412. In some embodiments, the controller 1402 can, for example using AI, map or determine relationships between changes in sensor data 1442 (e.g., changes in sensor readings) responsive to different levels of torque, force and/or velocity provided to a lower limb of a user through the exoskeleton boot 100 to predict how the user may react to a determined levels of torque, force and/or velocity in one or more current movements 1412 or future movements 1412. For example, the model 1446 can learn or identify patterns of a torque trajectory based in part on provided sensor data 1442 (e.g., powered data, unpowered data). The model 1446 can generate commands to apply torque through at least one exoskeleton boot 100 to a lower limb of a user. The model 1446 can receive subsequent or follow-up sensor data 1442 associated with a user performing movements 1412 using the exoskeleton boot 100 using the commands. The model 1446 can characterize the subsequent sensor data 1442 to determine, for example, if a current level of torque is sufficient or if a previously applied torque met a respective user's needs to perform the movement 1412. The controller 1402 can use the characterization to further train and update the model 1446, for example, for one or more subsequent movements 1412 performed by a user.

The commands can include instructions provided to one or more components of the exoskeleton boot 100 to generate a torque profile or a torque value of a series of torque values forming a torque profile. The controller 1402 can determine, based on the sensor data 1442 input into the model 1446 trained via a machine learning technique based on the sensor data 1442 (e.g., historical motion capture data) associated with one or more users performing one or more physical movements 1412, one or more commands for a second time interval subsequent to the first time interval. The model 1446 can generate the commands based in part on a movement 1412 the user is performing or is about to perform. For example, different movements 1412 can include different commands to augment a particular motion or movement of the user during the respective movement 1412. The commands can include or correspond to one or more torque profiles to be provided to the exoskeleton boot 100 that include torque values for the exoskeleton boot 100 to apply to a lower limb of the user to augment or aid the user in performing the subsequent or next movement 1412.

The controller 1402 and/or exoskeleton 100 can establish one or more connections 1450 to communicate with one or more other controllers 1402 (e.g., controllers of other exoskeleton devices) and/or one or more other exoskeleton boots 100. The connection 1450 can include a link, channel, or session between two or more controllers 1402 and/or two or more exoskeleton boots 100. The connection 1450 can include an encrypted and/or secure sessions established between two or more controllers 1402 and/or two or more exoskeleton boots 100. The encrypted connection 1450 can include an encrypted file, encrypted data or traffic transmitted between the between two or more controllers 1402 and/or two or more exoskeleton boots 100. In embodiments, the controller 1402 can include a communications interface to enable the controller 1402 to access a computer network such as a LAN, a WAN, or the Internet through a variety of wired and/or wireless or cellular connections, for example, to establish a connection 1450.

The connection 1450 can include a wireless connection or a wired connection. In embodiments, the controller 1402 can use data (e.g., sensor data 1442, calibration data 1434) received via wireless communication (e.g., wireless connection 1450) "as-is" or the controller 1402 may extrapolate the data based on the latency measurement and derivatives of the data. For example, in one embodiment, if a first exoskeleton boot 100 receives an ankle angle measurement of X degrees, an ankle velocity of Y degrees per ms, and measured a latency of Z ms, then the controller 1402 may use a calculated ankle value of X+(Y*Z) or determine a calculated ankle value for generating one or more torque values for subsequent movements 1412 performed by a user wearing the first exoskeleton boot 100.

The exoskeleton boot 100 can include a wireless interface 1444 to communicate with one or more other exoskeletons boot 100. The wireless interface 1444 can establish one or more wireless connections 1450 between one or more other exoskeletons boots 100, for example, to a wireless interface 1444 of the other exoskeleton boot 100 to communicate one or more packets 1410. The wireless interface 1444 can establish one or more wireless connections 1450 between one or more client devices. The wireless interface 1444 can include a network interface controller to connect to the network 1460 for the respective exoskeleton boot 100 to receive data and/or transmit data to a client device, controller, administrator device and/or other exoskeleton boot 100. The wireless interface 1444 can include or be implemented as a network driver, wireless driver, Bluetooth device, or a WiFi driver for the exoskeleton boot 100. The network 1460 can include one or more private networks such as a local area network (LAN) or a company Intranet, and/or a public network, such as a wide area network (WAN) or the Internet.

The controller 1402 can generate commands for an exoskeleton boot 100. The commands can include an instruction, task or function provided to an exoskeleton boot 100 to instruct the exoskeleton boot 100 a level or amount of torque, force, velocity or a combination of torque, force and velocity (e.g., impedance) to generate to aid a user wearing the respective exoskeleton boot 100 in performing a movement 1412. In embodiments, the commands can include a data structure indicating a desired, requested or target torque, force and/or velocity level.

Figure 15:
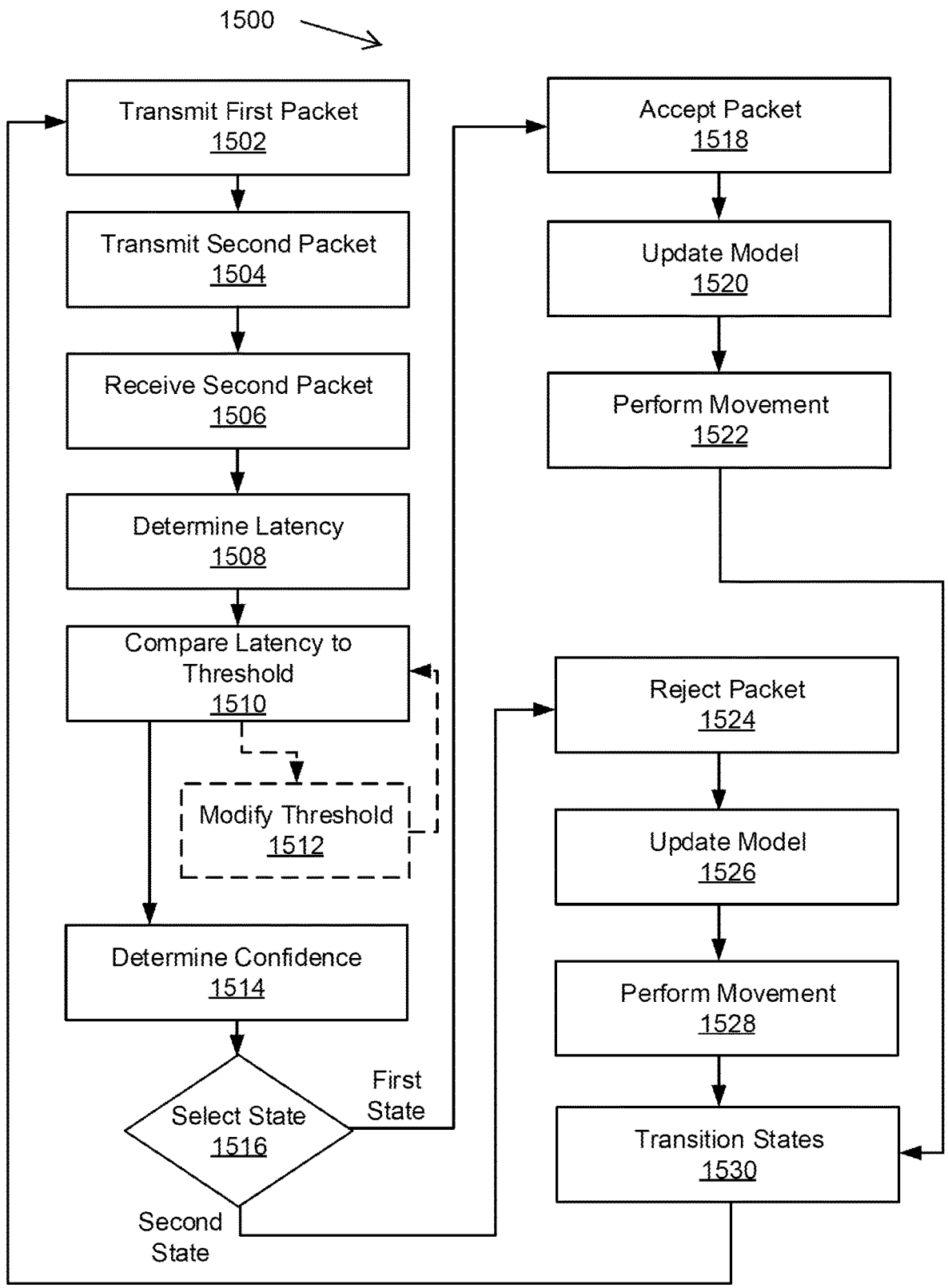
FIG. 15 illustrates a method of bilateral wireless communication between multiple exoskeleton devices in accordance with an illustrative embodiment.

Referring now to FIG. 15, depicted is a flow diagram of one embodiment of a method 1500 for method of bilateral wireless communication between multiple exoskeleton devices 100. In brief overview, the method 1500 can include one or more of: transmitting a first packet (1502), transmitting a second packet (1504), receiving a second packet (1506), determining a latency (1508), comparing the latency to a threshold (1510), modifying a threshold (1512), determining a confidence factor (1514), selecting a state (1516), accepting the packet (1518), updating a model (1520), performing a movement using data from multiple exoskeletons (1522), reject the packet (1524), updating a model (1526), performing a movement (1528), and transitioning states (1530). The functionalities of the method 1500 may be implemented using, or performed by, the components detailed herein in connection with FIGS. 1-14.

Referring now to operation (1502), and in some embodiments, a first packet 1410 can be transmitted by a first exoskeleton boot 100 (e.g., lower limb exoskeleton, boot exoskeleton) to a second exoskeleton boot 100, for example, through or via a connection 1450 between the first exoskeleton boot 100 and the second exoskeleton boot 100. The first exoskeleton boot 100 can transmit the first packet 1410 to one exoskeleton boot 100 (e.g., second exoskeleton boot 100) or multiple exoskeleton boots 100 (e.g., exoskeleton boots worn by multiple members of a group). The first packet 1410 can include a label or identifier 1432 (e.g., packet N) identifying the first exoskeleton boot 100 as the generator or originator of the first packet 1410. For example, the first exoskeleton boot 100 can insert or include the identifier 1432 in a header portion of the first packet 1410 and include instructions indicating to the receiving exoskeleton boot 100 to transmit a response packet 1410 to the first exoskeleton boot 100 and include the identifier 1432.

The first packet 1410 can include a time stamp 1430, the identifier 1432, sensor data 1442 (e.g., measurements 1442) and/or calibration data 1434 to calibrate communications between the first exoskeleton boot 100 and the second exoskeleton boot 100 or one or more other exoskeleton boots 100. The time stamp 1430 indicating a time the first packet 1410 was transmitted from the first exoskeleton boot 100. The identifier 1432 indicating the respective exoskeleton 100 the generated and transmitted the packet 1410. The sensor data 1442 can include any sensor data or measurement data described herein. The sensor data 1442 can include measurements, a gait state, joint angles, speed, and/or body positioning data, for example, associated with a user performing one or more movement 1412 wearing one or more exoskeleton boots 100. The calibration data 1434 can include information (e.g., bandwidth, data rate, type) on the connection 1450 between the first exoskeleton boot 100 and the second exoskeleton boot 100 and/or one or more other exoskeleton boots 100. The calibration data 1434 can include a pairing signal to establish and/or calibrate the connection 1450 between the first exoskeleton boot 100 and the second exoskeleton boot 100, for example, for a first or initial communication between the two exoskeleton boots 100.

The first packet 1410 can include a request for sensor data 1442 from one or more sensors 1440 connected to or coupled with the second exoskeleton boot 100. In some embodiments, the first packet 1410 can identify specific types of sensor data 1442, for example, but not limited to, ankle joint measurements during a running movement 1412 or torque data used during the running movement 1412. In some embodiments, the first packet 1410 can request sensor data 1442 associated with a current or active movement 1412 being performed by a user wearing one or more of the exoskeleton boots 100. In embodiments, the first packet 1410 can request all data or most recent sensor data 1442 (e.g., within a determined time range, generated since last packet communication) from the respective exoskeleton boot 100.

In embodiments, the first exoskeleton boot 100 can initiate a timer 1408 at the same time or substantially the same time the first exoskeleton boot 100 transmits the first packet 1410. For example, the first exoskeleton boot 100 can start or begin a timer 1408 to measure a response time for receiving a response to the first packet 1410 from the second exoskeleton boot 100. The timer 1408 can correspond to a time delay between transmitting a packet 1410 and receiving a response to the packet 1410. The timer 1408 can increment a counter or measure a time value until a response to the first packet 1410 is received.

Referring now to operation (1504), and in some embodiments, a second packet 1410 can be transmitted. The second exoskeleton boot 100 can receive the first packet 1410 (e.g., packet N) from the first exoskeleton boot 100. The second exoskeleton boot 100 can identify, extract or collect the information and/or metadata included with the first packet 1410, including but not limited to, the time stamp 1430, the identifier 1432, the sensor data 1442 and/or the calibration data 1434. The second exoskeleton boot 100 can use the identifier 1432 (e.g., label) from the first packet 1410 to determine that the first packet 1410 was transmitted by the first exoskeleton boot 100 and to transmit a response packet 1410 (e.g., second packet 1410) to the first exoskeleton boot 100.

The second exoskeleton boot 100 can generate a second packet 1410 (e.g., packet N+1) in response to the first packet 1410. The second packet 1410 can include a time stamp 1430, an identifier 1432, sensor data 1442 and/or calibration data 1434. The time stamp 1430 can correspond to a time when the second exoskeleton boot 100 transmits the second packet 1410. The identifier 1432 can identify the second exoskeleton boot 100 as generating and transmitting the second packet 1410. In embodiments, the second exoskeleton boot 100 can include a first identifier 1432 that is the identifier 1432 inserted by the first exoskeleton boot 100 and a second identifier 1432 associated with the second exoskeleton boot 100 and indicating that the second exoskeleton boot 100 generated and transmitted the second packet 141.

The second exoskeleton boot 100 can determine the requested sensor data 1442 and retrieve the requested sensor data 1442 from one or more sensors 1440 connected to or coupled with the second exoskeleton boot 100. The second exoskeleton boot 100 can read or obtain current or active sensor data 1442 from the sensors 1440. In some embodiments, the second exoskeleton boot 100 can transmit a request to the sensors 1440 identifying the sensor data 1442 requested by the first exoskeleton boot 100. In embodiments, the second exoskeleton boot 100 can retrieve the sensor data 1442 from a memory 1404 of the second exoskeleton boot 100. The second exoskeleton boot 100 can initiate a timer 1408 at the same time or substantially the same time the second exoskeleton boot 100 transmits the second packet 1410. The second exoskeleton boot 100 can start or begin the timer 1408 to measure a response time for receiving a response to the second packet 1410 from the first exoskeleton boot 100. The timer 1408 can increment a counter or measure a time value until a response to the second packet 1410 is received.

Referring now to operation (1506), and in some embodiments, a second packet 1410 can be received. The first exoskeleton boot 100 can, responsive to transmitting the first packet 1410, receive a second packet 1410 (e.g., packet N+1) from the second exoskeleton boot 100. The first exoskeleton boot 100 can identify, extract or collect the information and/or metadata included with the second packet 1410, including but not limited to, the time stamp 1430, the identifier 1432, the sensor data 1442 and/or the calibration data 1434. The first exoskeleton boot 100 can use the identifier 1432 included with the second packet 1410 to determine that the second packet 1410 is a response to the first packet 1410. The first exoskeleton boot 100 can stop the timer 1408 for the first packet 1410 responsive to receiving the second packet 1410 and determining the second packet 1410 is a response to the first packet 1410. In embodiments, the first exoskeleton boot 100 can stop the timer 1408 at the same time or substantially the same time the second packet 1410 is received. The timer 1408 can generate or provide a time difference between when the first packet 1410 was transmitted by the first exoskeleton boot 100 to the second exoskeleton boot 100 and the second packet 1410 was received at the first exoskeleton boot 100. The timer 1408 can include a time value, a time period, time range or counter value.

Referring now to operation (1508), and in some embodiments, a latency 1414 can be determined. The first exoskeleton boot 100 can determine a latency 1414 for communication between the first exoskeleton boot 100 and the second exoskeleton boot 100 based on a time difference between transmission of the first packet 1410 and receipt of the second packet 1410 or the value of the timer 1408. The latency 1414 can include or correspond to a time value for the for the first exoskeleton boot 100 to transmit a packet 1410 and receive a response (e.g., second packet) from the second exoskeleton boot 100 or a how long it takes the first exoskeleton boot 100 to receive a next or subsequent correctly labeled packet 1410 (e.g., response to first packet 1410). The latency 1414 can include or correspond to a time interval, time delay or time difference between the transmission of the first packet 1410 by the first exoskeleton boot 100 and receipt of the second packet 1410 at the first exoskeleton boot 100.

The first exoskeleton boot 100 can use the value of the timer 1408 to determine the latency 1414. In some embodiments, the value of the timer 1408 can correspond to the latency 1414 between the first exoskeleton boot 100 and the second exoskeleton boot 100. The first exoskeleton boot 100 can verify the latency 1414, for example, using the time stamps 1430 of the first packet 1410 and the second packet 1410. The first exoskeleton boot 100 can retrieve the time stamp 1430 of the first packet 1410 and compare the time stamp 1430 of the first packet 1410 to a time of receipt of the second packet 1410 to determine the latency 1414 or the time difference between transmission of the first packet 1410 and receipt of the second packet 1410. The first exoskeleton boot 100 can retrieve the time stamp 1430 of the first packet 1410 and retrieve the time stamp 1430 of the second packet 1410. The first exoskeleton boot 100 can compare the time stamp 1430 of the first packet 1410 to the time stamp 1430 of the second packet 1410 to determine the time difference between transmission of the first packet 1410 and receipt of the second packet 1410.

Referring now to operation (1510), and in some embodiments, the latency 1414 can be compared to a threshold 1416. The first exoskeleton boot 100 can compare the determined latency 1414 to a threshold 1416 (e.g., latency threshold) to determine if the latency 1414 is acceptable (e.g., less than the threshold, with an acceptable range) or unacceptable (e.g., greater than the threshold, outside an acceptable range). The threshold 1416 can include or correspond to a time value or time range indicating an acceptable latency 1414 or an unacceptable latency 1414. For example, the first exoskeleton boot 100 can compare the determined latency 1414 to the threshold 1416 and if the latency 1414 is less than the threshold 1416, the first exoskeleton boot 100 determine the latency 1414 is acceptable or within an allowable range. A latency 1414 that is less than the threshold 1416 can indicate an acceptable time delay between transmission of a packet 1410 and receipt of a response. The first exoskeleton boot 100 can compare the determined latency 1414 to the threshold 1416 and if the latency 1414 is greater than the threshold 1416, the first exoskeleton boot 100 determine the latency 1414 is unacceptable or not within an allowable range. A latency 1414 that is greater than the threshold 1416 can indicate too great of a time delay to accept or trust data included within a packet 1410.

Referring now to operation (1512), and in some embodiments, the threshold 1416 can be modified. In some embodiments, the first exoskeleton boot 100 can use the type of sensor data 1442 included with the second packet 1410 to determine if the current threshold 1416 is accurate or appropriate for a current or active movement 1412 a user is performing or about to perform. If the first exoskeleton boot 100 determines that the current threshold 1416 is accurate or appropriate, the method 1500 can move to (1514) to determine a confidence factor. In some embodiments, the first exoskeleton boot 100 may not make a determination if the current threshold 1416 is accurate or appropriate and the method 1500 can move from (1510) to (1514) to determine a confidence factor. If the first exoskeleton boot 100 determines that the current threshold 1416 is not accurate or not appropriate, the first exoskeleton boot 100 can modify the threshold 1416 based on a type of activity represented by sensor data 1442 included with the second packet 1410.

The first exoskeleton boot 100 can modify the threshold 1416 based on a type of gait event 1413 associated with the data of the second packet 1410. For example, the threshold 1416 can include a variable threshold 1416 that is determined, selected or based at least in part on a type of data (e.g., temperature data, activity data, gait data), a type of gait event 1413, a type of movement 1412 (e.g., leg swing, plantarflexion, dorsiflexion) and/or type of activity (e.g., walking, running, sitting). Some movements 1412, such as but not limited to running, may use immediate or faster response times between sensor data 1442 to perform the respective movement 1412 and thus, a lower latency 1414 is used or accepted as compared to other movements. Some movements 1412, such as but not limited to running can be performed with more delay or lag between the and thus, a greater or increased communication latency 1414 can be accepted or dealt with to perform the respective movement 1412. The first exoskeleton boot 100 can modify the threshold 1416 based at least in part on the type of data, the type of movement 1412 and/or the type of activity.

The first exoskeleton boot 100 can receive the second packet 1410 and determine the type of sensor data 1442 included within the packet 1410, a type of gait event 1413, a type of movement 1412 identified in the packet 1410 and/or a type of activity identified in the packet 1410. The first exoskeleton boot 100 can modify the threshold 1416 based at least in part on the type of data, the type of gate event 1413, the type of movement 1412 and/or the type of activity. In some embodiments, the thresholds 1416 can be stored and/or maintained in a storage device or memory 1404 of the first exoskeleton boot 100 and the first exoskeleton boot 100 can use the determined the type of data, the type of movement 1412 and/or the type of activity identified in the packet 1410 to select to corresponding or appropriate threshold 1416 for the respective packet 1410. The method 1500 can return to (1510) to compare the latency 1414 of the packet 1410 to the modified or selected threshold 1416 if the threshold 1416 is modified or a new threshold 1416 is selected.

Referring now to operation (1514), and in some embodiments, a confidence factor 1418 can be determined. The first exoskeleton boot 100 can determine a confidence factor 1418 (e.g., confidence level, confidence score, confidence threshold) for the second packet 1410 based in part on the time value associated with the second packet 1410. The confidence factor 1418 can indicate a trust level or confidence in sensor data 1442 received with the second packet 1410. The confidence factor 1418 can include a weighting value applied to data from the second packet 1410 to increase a weight or importance of more recent or newer data and decrease a weight or importance of older data. For example, a long delay between communications between different partner devices (e.g., first exoskeleton boot 100, second exoskeleton boot 100) can indicate an issue with at least one of the partner devices and can result in a lower confidence factor 1418. A short delay between communications between different partner devices (e.g., first exoskeleton boot 100, second exoskeleton boot 100) can indicate a strong connection between the partner devices, that the devices are functioning properly and can result in a greater confidence factor 1418.

The first exoskeleton boot 100 can determine the confidence factor for the second packet 1410 based on a time difference between the second packet 1410 and one or more previous packets 1410 accepted from the second exoskeleton boot 100. For example, the first exoskeleton boot 100 can determine a time value for the last valid or accepted packet 1410 from the second exoskeleton boot 100. The first exoskeleton boot 100 can determine the time difference between the time value for the last valid or accepted packet 1410 from the second exoskeleton boot 100 and the time value for the current or more recent packet 1410 (e.g., second packet 1410) from the second exoskeleton boot 100. The first exoskeleton boot 100 can assign the second packet 1410 a confidence factor 1418 based in the determined time difference. The confidence factor 1418 can correspond to the time difference or be a percentage of the time difference such that a greater confidence factor 1418 can be applied or assigned to a lower time difference and a lower confidence factor 1418 can be applied or assigned to a greater time difference.

Referring now to operation (1516), and in some embodiments, a state 1420 can be selected. The first exoskeleton boot 100 can select a state 1420 responsive to the comparison of the latency 1414 to the threshold 1416 and/or the confidence factor 1418. The first exoskeleton boot 100 can accept, based on the selected state 1420, data from the second packet 1410 or reject, based on the selected state 1420, data from the second packet 1410. The selected state 1420 include a communications state to control or indicate whether the first exoskeleton boot 100 trusts or accepts data from a partner device (e.g., second exoskeleton boot 100) or does not accept and/or discards data from a partner device (e.g., second exoskeleton boot 100). In embodiments, if the measured communication latency 1414 is less than or below the threshold 1416, the first exoskeleton boot 100 can determine that the data from second packet 1410 is valid. The first exoskeleton boot 100 can determine that the measured communication latency 1414 is less than or below the threshold 1416 and the confidence factor 1418 is above a confidence threshold and determine that the sensor data 1442 from second packet 1410 is valid. The first exoskeleton boot 100 can select or implement a first state 1420 indicating that second packet 1410 is valid and data received with the second packet 1410 is valid. In the first state 1420, the first exoskeleton boot 100 can accept the second packet 1410 and data received with the second packet 1410 and use the data to perform one or more movements 1412.

In embodiments, if the measured communication latency 1414 is greater than the threshold 1416, the first exoskeleton boot 1410 can determine that the data from second packet 1410 is not valid (e.g., too old, outdated). In some embodiments, the first exoskeleton boot 100 can determine that the measured communication latency 1414 is less than or below the threshold 1416 but the confidence factor 1418 is less than a confidence threshold and determine that the sensor data 1442 from second packet 1410 is not valid. The first exoskeleton boot 100 can select or implement a second state 1420 indicating that second packet 1410 is not valid and data received with the second packet 1410 is not valid. In the second state 1420, the first exoskeleton boot 100 can reject, ignore or discard the second packet 1410 and data received with the second packet 1410. In embodiments, in the second state, the first exoskeleton boot 100 may not use data from a partner device (e.g., second exoskeleton boot 100).

Referring now to operation (1518), and in some embodiments, the first exoskeleton boot 100 can determine to accept the second packet 1410. The first exoskeleton 100 can determine responsive to the comparison of the latency 1414 to the threshold 1416 and/or the selected state 1420, whether to accept or reject the second packet 1410 from the second exoskeleton boot 100. For example, if the latency 1414 is less than the threshold 1416, the first exoskeleton boot 100 can determine that the second packet 1410 is valid and accept data received with the second packet 1410. In some embodiments, the first exoskeleton boot 100 can determine that the first exoskeleton boot 100 is executing in a first state 1420 and determine that the second packet 1410 is valid and accept data received with the second packet 1410 based on the first state 1420. If the first exoskeleton boot 100 determines to accept the second packet 1410, the method 1500 can move to (1520) to update a model 1446 using data from the second packet 1410.

Referring now to operation (1520), and in some embodiments, a model 1446 can be updated. The first exoskeleton boot 100 can update, responsive to the comparison, a model 1446 indicating data weighted based on the latency 1414 for controlling the first exoskeleton boot 100 and the second exoskeleton boot 100. In some embodiments, the first exoskeleton boot 100 can update, responsive to the determination to accept the second packet 1410, a model 1446 indicating data accepted for controlling the first exoskeleton boot 100 and/or the second exoskeleton boot 100. The model 1446 can generate commands or control parameters to instruct the exoskeleton boot 100 on a level of torque or force to provide to perform a movement 1412 based on received sensor data 1442 from the first exoskeleton boot 100 and/or from a different exoskeleton boot 100 through one or more accepted packets 1410. The model 1446 can maintain a database of accepted data values and update, for example in real-time, the data values as new or subsequent sensor data 1442 from the first exoskeleton boot 100 and/or subsequent data from one or more different exoskeleton boot 100 through one or more accepted packets 1410. The controller 1402 can, if the second packet 1410 is accepted, provide the data from the second packet 1410 to the model 1446 to update the model 1446 with the data from the second packet 1410.

The model 1446 can include or execute a machine learning model (e.g., artificial intelligence model) trained using training data, sensor data 1442 and/or data included in one or more packets 1410 to generate one or more commands to perform a movement 1412. In embodiments, the controller 1402 can provide the sensor data 1442 from one or more sensors 1440 connected to the first exoskeleton boot 100 and data (e.g., sensor data 1442) from one or more packets 1410 (e.g., second packet 1410) from other exoskeleton boots 100 as inputs to the machine learning model 1446 to cause the model 1446 to generate commands (e.g., control parameters) for performing one or more movements 1412. The controller 1402 can update the model 1446 in real-time, for example, as additional sensor data 1442 and data from one or more packets 1410 is received and accepted. The output from the model 1446 can include, but is not limited to, torque values, power values, force values and/or speed values. The controller 1402 can receive the output from the model 1446 and use the output to continue a current movement 1412 and/or to perform one or more next or subsequent movements 1412 using the exoskeleton boot 100.

Referring now to operation (1522), and in some embodiments, a movement 1412 can be performed using data from the second packet 1410 and/or output from the model 1446. The first exoskeleton boot 100 can generate, using data from the mode 1446, a command to cause an electric motor 1105 of the first exoskeleton boot 100 to generate torque to aid a limb of a user in performing a movement 1412. The first exoskeleton boot 100 can perform a movement 1412, continue a movement 1412 and/or perform a series of movements 1412 based in part on commands generated by the controller 1402 and responsive to the determination to accept the second packet 1410. The first exoskeleton boot 100 can use sensor data 1442 from multiple different sources (e.g., multiple exoskeleton boots 100) to determine and calculate appropriate torque values, force values and/or power values to provide to a user through the first exoskeleton boot 100 and aid the user in performing the movement 1412. The first exoskeleton boot 100 can use sensor data 1442 from multiple different sources to determine a current or active status of the user, including but not limited to, a current gait stance, running speed, walking speed, leg swing speed, ankle angle measurements and/or knee angle measurements. The first exoskeleton boot 100 can use sensor data 1442 from multiple different sources to determine a next or subsequent torque value (or force or power) to provide to a user through the first exoskeleton boot 100 to continue a current movement 1412 (e.g., user actively performing) or a next, subsequent movement 1412, including but not limited to, a gait event 1413, modify a running speed, modify a walking speed, modify a leg swing speed, modify an ankle angle and/or knee angle of the user. For example, in one embodiment and based in part on a current ankle angle measurement at the first exoskeleton boot 100 and the second exoskeleton boot 100, the first exoskeleton boot 100 can determine a torque value for the first exoskeleton boot 100 to provide to a lower limb of the user to complete a current movement 1412 or transition from a first movement 1412 to a second, different movement 1412 (e.g., transition from sitting to standing, walking to running). The use of sensor data 1442 can provide a more accurate reflection of a current or active status of the user and enable the first exoskeleton boot 100 to determine appropriate torque values, force values and/or power values to provide to a user through the first exoskeleton boot 100 and aid the user in performing the movement 1412.

The first exoskeleton boot 100 can, using the sensor data 1442 from the first exoskeleton boot 100 and the second exoskeleton boot 100, generate commands to indicating a desired, requested or target torque, force and/or velocity level. The commands can include one or more torque values for the first exoskeleton boot 100 to apply to a lower limb of the user to augment or aid the user in performing the movement 1412. In embodiments, the controller 1402 can receive the sensor data 1442 from the first exoskeleton boot 100 and the second exoskeleton boot 100 and generate commands for the first exoskeleton boot 100 to control the operation of the first exoskeleton boot 100, for example, in real-time as a user is performing one or more movements 1412 based in part on real-time data (e.g., sensor data 1442) associated with the user performing the one or more movements 1412 to augment and aid the user through the first exoskeleton boot 100 in performing the movements 1412. The controller 1402 can update or modify commands indicating torque to be applied to a limb of the user through the first exoskeleton boot based in part on feedback as the user is performing the movement 1412 or a previous movement 1412. The controller 1402 can generate commands to correct or provide a desired level of torque or force through the first exoskeleton boot 100 to aid the user in performing the movements 1412 at the correct or appropriate time, for example, using the real-time feedback. The controller 1402 can generate commands to account for different types of people (e.g., age, size, ability, etc.), different types of gait (e.g., walking, running, jumping, etc.), different terrains (e.g., pavement, grass, sand, ice, etc.), different speeds (e.g., slow, medium, fast, etc.), different target power levels (e.g., high augmentation, transparent, low, etc.) based on the received sensor data 1442.

Referring now to operation (1524), and in some embodiments, the first exoskeleton boot 100 can determine to reject the second packet 1410. The first exoskeleton 100 can determine responsive to the comparison of the latency 1414 to the threshold 1416 and/or the selected state 1420, whether to accept or reject the second packet 1410 from the second exoskeleton boot 100. If the latency 1414 is greater than the threshold 1416, the first exoskeleton boot 100 can determine that the second packet 1410 is not valid and reject the second packet 1410 and data received with the second packet 1410. The first exoskeleton boot 100 can determine that the first exoskeleton boot 100 is executing in a second state 1420 and determine that the second packet 1410 is not valid and reject the second packet 1410 and data received with the second packet 1410 based on the second state 1420. If the first exoskeleton boot 100 determines to reject the second packet 1410, the method 1500 can move to (1524) to update a model 1446 using data from one or more sensors 1440 connected to the first exoskeleton boot 100.

Referring now to operation (1526), and in some embodiments, a model 1446 can be updated. The first exoskeleton boot 100 can update, responsive to the comparison, a model 1446 indicating data weighted based on the latency 1414 for controlling the first exoskeleton boot 100 and the second exoskeleton boot 100. In some embodiments, the first exoskeleton boot 100 can update, responsive to the determination to reject the second packet 1410, a model 1446 indicating data accepted for controlling the first exoskeleton boot 100 and/or the second exoskeleton boot 100. The model 1446 can generate commands or control parameters to instruct the exoskeleton boot 100 on a level of torque or force to provide to perform a movement 1412 based on received sensor data 1442 from the first exoskeleton boot 100. The model 1446 can maintain a database of accepted data values and update, for example in real-time, the data values as new or subsequent sensor data 1442 from the first exoskeleton boot 100. The controller 1402 can provide the sensor data 1442 from one or more sensors 1440 connected to the first exoskeleton boot 100 to the model 1446 to update the model 1446 with the sensor data 1442.

The model 1446 can include or execute a machine learning model (e.g., artificial intelligence model) trained using training data, sensor data 1442 and/or data included in one or more packets 1410 to generate one or more commands to perform a movement 1412. In embodiments, the controller 1402 can provide the sensor data 1442 from one or more sensors 1440 connected to the first exoskeleton boot 100 as inputs to the machine learning model 1446 to cause the model 1446 to generate commands (e.g., control parameters) for performing one or more movements 1412. The controller 1402 can update the model 1446 in real-time, for example, as additional sensor data 1442 is received and accepted. The output from the model 1446 can include, but is not limited to, torque values, power values, force values and/or speed values. The controller 1402 can receive the output from the model 1446 and use the output to continue a current movement 1412 and/or to perform one or more next or subsequent movements 1412 using the exoskeleton boot 100.

Referring now to operation (1528), and in some embodiments, a movement 1412 can be performed. The first exoskeleton boot 100 can generate, using data from the mode 1446, a command to cause an electric motor 1105 of the first exoskeleton boot 100 to generate torque to aid a limb of a user in performing a movement 1412. The first exoskeleton boot 100 can perform a movement 1412, continue a movement 1412 and/or perform a series of movements 1412 based in part on commands generated by the controller 1402 and responsive to the determination to reject the second packet 1410. The first exoskeleton boot 100 can perform the movement 1412 using data or measurements received by the first exoskeleton boot 100 and/or sensors 1440 connected to the first exoskeleton boot 100. In some embodiments, the first exoskeleton boot 100 can perform the movement 1412 not using data or measurements received from the second exoskeleton boot 100 and/or sensors 1440 connected to the second exoskeleton boot 100, for example, responsive to rejecting one or more packets 1410 from the second exoskeleton boot 100. The first exoskeleton boot 100 can determine that the sensor data 1442 from the second exoskeleton boot 100 may be unreliable or old and thus inaccurate to use to generate commands to perform a movement 1412, continue a movement 1412 and/or perform a series of movements 1412. For example, in one embodiment, if the user is running and the sensor data 1442 is late or the connection 1450 between the first exoskeleton boot 100 and the second exoskeleton boot 100 has high latency 1414, the ankle angle measurements from the second exoskeleton boot 100 may be inaccurate or not accurately reflect a current position of the user. If the first exoskeleton boot 100 uses the old data to generate new commands, the calculated torque may be inappropriate for a current positon of the user or current speed of the user wearing the first exoskeleton boot 100.

The first exoskeleton boot 100 can perform a movement 1412, continue a movement 1412 and/or perform a series of movements 1412 using the first exoskeleton boot 100 responsive to the determination to reject the second packet 1410. The first exoskeleton boot 100 and/or controller 1402 can use sensor data 1442 obtained from one or more sensors 1440 connected to or coupled with the first exoskeleton boot 100. In embodiments, the first exoskeleton boot 100 and/or controller 1402 can use historical sensor data 1442 maintained in the memory 1404 and associated with the same user performing the same movement 1412 or similar movement 1412 previously and generate predictions based on the historical sensor data 1442 and current sensor data 1442 obtained from one or more sensors 1440 connected to or coupled with the first exoskeleton boot 100. The first exoskeleton boot 100 and/or controller 1402 can determine and calculate appropriate torque values, force values and/or power values to provide to a user through the first exoskeleton boot 100 and aid the user in performing the movement 1412. The first exoskeleton boot 100 and/or controller 1402 can determine a current or active status of the user, including but not limited to, a current gait stance, running speed, walking speed, leg swing speed, ankle angle measurements and/or knee angle measurements. The first exoskeleton boot 100 and/or controller can determine a next or subsequent torque value (or force or power) to provide to a user through the first exoskeleton boot 100 to continue a current movement 1412 (e.g., user actively performing) or a next, subsequent movement 1412, including but not limited to, a gait event 1413, modify a running speed, modify a walking speed, modify a leg swing speed, modify an ankle angle and/or knee angle of the user.

Referring now to operation (1530), and in some embodiments, the first exoskeleton boot 100 can transition states 1420. The first exoskeleton boot 100 can transition between a first state 1420 and a second state 1420 responsive to a comparison of the latency 1414 of packet 1410 to the threshold 1416. In embodiments, the first exoskeleton boot 100 can transition, using sensor data 1442 from the second packet 1410 or based on data from the second packet 1410, from the first state 1420 to the second state 1420. The first exoskeleton boot 100 can be in the first state 1420 and determine that the latency 1414 of packet 1410 is greater than the threshold 1416 and transition from the first state 1420 to the second state 1420. The first exoskeleton boot 100 can maintain, using sensor data 1442 from the second packet 1410 or based on data from the second packet 1410, a current state 1420 (e.g., first state 1420, second state 1420). For example, the first exoskeleton boot 100 can be in the first state 1420 and determine that the latency 1414 of packet 1410 is less than the threshold 1416 and maintain the first state 1420. The first exoskeleton boot 100 can be in the second state 1420 and determine that the latency 1414 of packet 1410 is greater than the threshold 1416 and maintain the second state 1420. In some embodiments, the first exoskeleton boot 100 can transition, using data from the second packet 1410 or based on sensor data 1442 from the second packet 1410, from the second state 1420 to the first state 1420. The first exoskeleton boot 100 can be in the second state 1420 and determine that the latency 1414 of packet 1410 is less than the threshold 1416 and transition from the second state 1420 to the first state 1420. The method 1500 can return to (1502) to transmit one or more subsequent packets 1410 and verify or determine a current communication latency 1414 between the respective exoskeleton boots 100.

Figure 16:
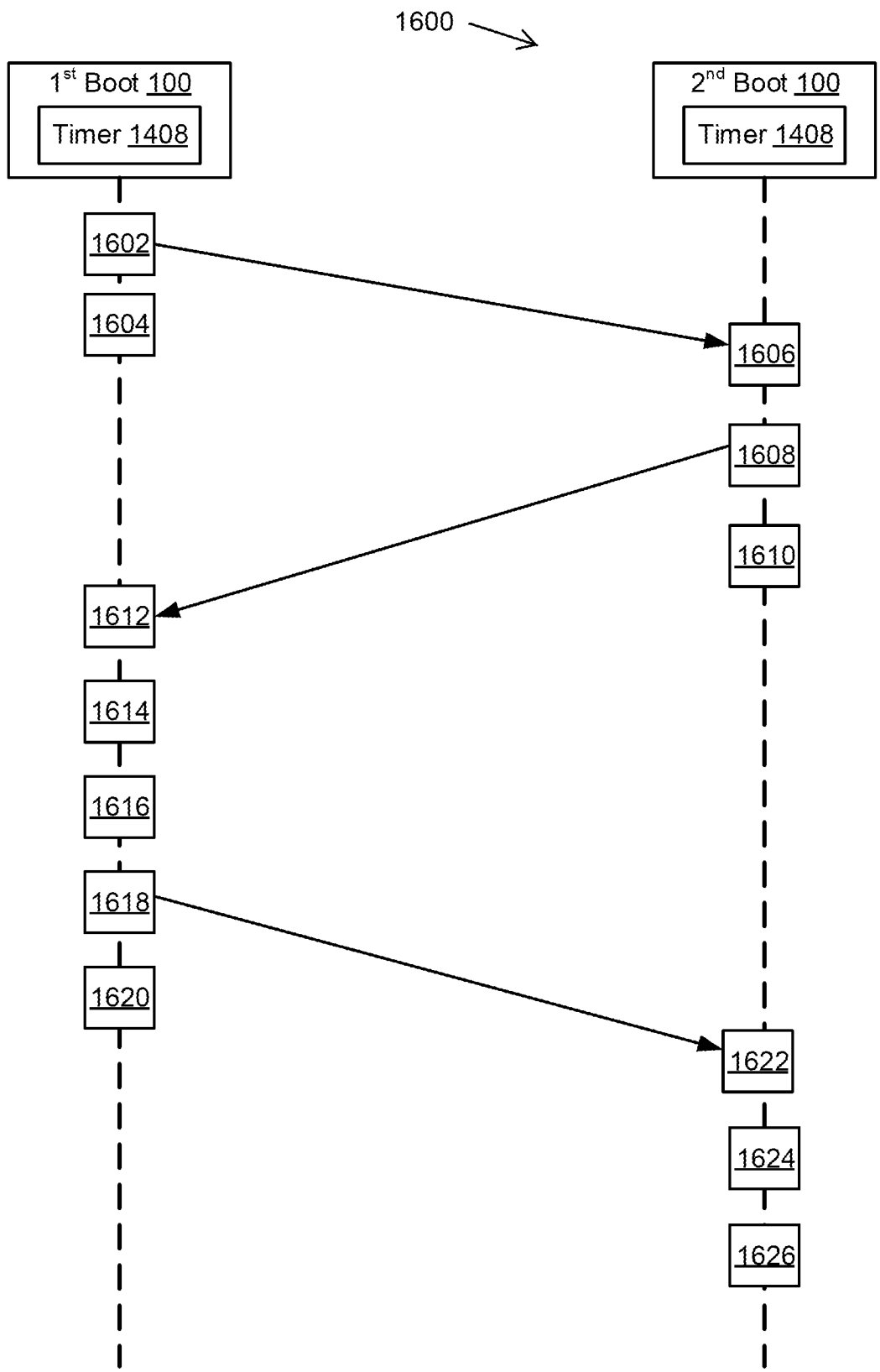
FIG. 16 illustrates a method of determining latency for communications between multiple exoskeleton devices in accordance with an illustrative embodiment.

Referring now to FIG. 16, depicted is a flow diagram of one embodiment of a method 1600 for method of determining latency for communications between multiple exoskeleton devices. In embodiments, a first exoskeleton boot 100 can transmit a labeled packet 1410 to one or more other exoskeleton boots 100 and determine how long it takes to receive a next correctly labeled packet 1410 from at least one of the other one or more exoskeleton boots 100. If the response time or determined latency 1414 is within a specific range, such as less than a threshold 1416, the received packet 1410 can be deemed valid and data included with the packet 1410 can be used the first exoskeleton boot 100 for making calculations to perform one or more subsequent movements 1412. The data from the accepted packet 1410 can be provided as an input to a model 1446 to determine commands or control parameters indicating torque levels or force levels for the exoskeleton boot 100. In some embodiments, the exoskeleton boots 100 can be configured in a master/slave configuration with the transmitting or measuring exoskeleton boot 100 indicated as the master node and the responding exoskeleton boots 100 indicated as the slave nodes. Thus, each exoskeleton boot 100 may perform as a master node, for example, when transmitting a packet 1410 to one or more other exoskeleton boots 100 and may perform as a slave node, for example, when receiving a packet 1410. The functionalities of the method 1600 may be implemented using, or performed by, the components detailed herein in connection with FIGS. 1-14.

Referring now to operation (1602), and in some embodiments, a first exoskeleton boot 100 can transmit a first packet 1410 to a second exoskeleton boot 100 or multiple different exoskeleton boots 100. The first packet 1410 can include or correspond to a labeled packet 1410 having a label or identifier 1432 indicating the packet 1410 was transmitted by the first exoskeleton boot 100 and a response to the first packet 1410 or next packet 1410 should be transmitted back to the first exoskeleton boot 100. In embodiments, the labeled packet 1410 can include instructions or commands instructing the receiving exoskeleton boot 10 to transmit the response or next packet 1410 to the transmitting exoskeleton boot 100, here the first exoskeleton boot 100.

Referring now to operation (1604), and in some embodiments, the first exoskeleton boot 100 can start or begin a timer 1408. The first exoskeleton boot 100 can start the timer 1408 as the first packet 1410 is transmitted, for example, simultaneously with transmitting the first packet 1410. The timer 1408 can measure a time value indicating a time to receive a response or next packet 1410 in response to the first packet 1410 and/or a time delay between transmitting the first packet and receiving a next packet 1410 in response to the first packet 1410. The first exoskeleton boot 100 can run or execute timer 1408 until a response or next packet 1410 is received in response to the first packet 1410.

Referring now to operation (1606), and in some embodiments, a second exoskeleton boot 100 can receive the first packet 1410 (e.g., labeled packet). The first packet 1410 can include the identifier 1432 indicating the first packet 1410 was transmitted by the first exoskeleton boot 100. Referring now to operation (1608), and in some embodiments, the second exoskeleton boot 100 can transmit a second packet 1410 to the first exoskeleton boot 100. The second packet 1410 can include or correspond to a labeled packet 1410 having a label or identifier 1432 indicating the packet 1410 was transmitted by the second exoskeleton boot 100. In embodiments, the second packet 1410 can be labeled to indicate that the second packet 1410 is a response to the first packet 1410. For example, the second packet 1410 may keep or maintain the original label or identifier 1432 included by the first exoskeleton boot 100 such that the first exoskeleton boot 100 can determine that the second packet 1410 is a response to the first packet 1410.

Referring now to operation (1610), and in some embodiments, the second exoskeleton boot 100 can start or begin a timer 1408. The second exoskeleton boot 100 can start the timer 1408 as the second packet 1410 is transmitted, for example, simultaneously with transmitting the second packet 1410. The second exoskeleton boot 100 can run or execute timer 1408 until a response or next packet 1410 is received in response to the second packet 1410. Referring now to operation (1612), and in some embodiments, the first exoskeleton boot 100 can receive can receive the second packet 1410 (e.g., labeled packet). The second packet 1410 can include the identifier 1432 indicating the second packet 1410 was transmitted by the second exoskeleton boot 100 and is a response to the first packet 1410 transmitted by the first exoskeleton boot 100.

Referring now to operation (1614), and in some embodiments, the first exoskeleton boot 100 can stop the timer 1408. The first exoskeleton boot 100 can stop the timer 1408 as the second packet 1410 is received and determined to be a response to the first packet 1410, for example, simultaneously with receiving the second packet 1410. The first exoskeleton boot 100 can measure the value of the timer 1408 that indicates the time it took to receive a response or next packet 1410 in response to the first packet 1410. The first exoskeleton boot 100 can determine the latency 1414 for communications between the first exoskeleton boot 100 and the second exoskeleton boot 100 using the value of the timer 1408.

Referring now to operation (1616), and in some embodiments, the first exoskeleton boot 100 can accept the second packet 1410 based on the determined latency 1414. In embodiments, the first exoskeleton boot 100 can assume, based on the latency being less than the value of the timer 1408 and/or the determined latency 1414, that the second packet 1410 is from a determined time (e.g., assume packet is from (timer A/2) seconds ago). In some embodiments, the first exoskeleton boot 100 can compare the latency 1414 to a threshold 1416 to determine if the second packet 1410 and the data received with the second packet 1410 is valid and trustworthy. The first exoskeleton boot 100 can accept the second packet 1410 if the latency 1414 is less than the threshold 1416 or reject the second packet 1410 if the latency 1414 is greater than the threshold 1416.

Referring now to operation (1618), and in some embodiments, the first exoskeleton boot 100 can transmit a third packet 1410 to the second exoskeleton boot 100. The third packet 1410 can be a response to the second packet 1410 received from the second exoskeleton boot 100. The third packet 1410 can include or correspond to a labeled packet 1410 having a label or identifier 1432 indicating the packet 1410 was transmitted by the first exoskeleton boot 100. In embodiments, the third packet 1410 can be labeled to indicate that the third packet 1410 is a response to the second packet 1410. For example, the third packet 1410 may keep or maintain the label or identifier 1432 included by the second exoskeleton boot 100 such that the second exoskeleton boot 100 can determine that the third packet 1410 is a response to the second packet 1410.

Referring now to operation (1620), and in some embodiments, the first exoskeleton boot 100 can start or begin a timer 1408 for the third packet 1410. The first exoskeleton boot 100 can start the timer 1408 as the third packet 1410 is transmitted, for example, simultaneously with transmitting the third packet 1410. Referring now to operation (1622), and in some embodiments, the second exoskeleton boot 100 can receive the third packet 1410 (e.g., labeled packet). The third packet 1410 can include the identifier 1432 indicating the third packet 1410 was transmitted by the first exoskeleton boot 100 and/or a label or identifier 1432 indicating that the third packet 1410 is a response to the second packet 1410 transmitted by the second exoskeleton boot 100.

Referring now to operation (1624), and in some embodiments, the second exoskeleton boot 100 can stop the timer 1408 for the second packet 1410. The second exoskeleton boot 100 can stop the timer 1408 as the third packet 1410 is received and determined to be a response to the second packet 1410, for example, simultaneously with receiving the third packet 1410. The second exoskeleton boot 100 can measure the value of the timer 1408 that indicates the time it took to receive a response or next packet 1410 in response to the second packet 1410. The second exoskeleton boot 100 can determine the latency 1414 for communications between the first exoskeleton boot 100 and the second exoskeleton boot 100 using the value of the timer 1408 for the second packet 1410.

Referring now to operation (1626), and in some embodiments, the second exoskeleton boot 100 can accept the third packet 1410 based on the determined latency 1414. In embodiments, the second exoskeleton boot 100 can assume or determine, based on the value of the timer 1408 and/or the determined latency 1414, that the third packet 1410 is from a determined time (e.g., assume packet is from (timer B/2) seconds ago). In some embodiments, the second exoskeleton boot 100 can compare the latency 1414 to a threshold 1416 to determine if the third packet 1410 and the data received with the third packet 1410 is valid and trustworthy. The second exoskeleton boot 100 can accept the third packet 1410 if the latency 1414 is less than the threshold 1416 or reject the third packet 1410 if the latency 1414 is greater than the threshold 1416. The method 1600 can return to (1602) to communicate subsequent packets 1410 between the exoskeleton boots 100.

Embodiments of the subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices).

The operations described in this specification can be performed by a data processing apparatus on data stored on one or more computer-readable storage devices or received from other sources. The term "data processing apparatus" or "computing device" encompasses various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a circuit, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more circuits, subprograms, or portions of code). A computer program can be deployed to be executed on one computer or on multiple computers that are located at one site or distributed across multiple sites and interconnected by a communication network.

Processors suitable for the execution of a computer program include, by way of example, microprocessors, and any one or more processors of a digital computer. A processor can receive instructions and data from a read only memory or a random access memory or both. The elements of a computer are a processor for performing actions in accordance with instructions and one or more memory devices for storing instructions and data. A computer can include, or be operatively coupled to receive data from or transfer data to, or both, one or more mass storage devices for storing data, e.g., magnetic, magneto optical disks, or optical disks. A computer need not have such devices. Moreover, a computer can be embedded in another device, e.g., a personal digital assistant (PDA), a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The implementations described herein can be implemented in any of numerous ways including, for example, using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to or receive communications from other devices. The display unit(s) may be provided, for example, to allow a user to view various information in connection with execution of the instructions. The user input device(s) may be provided, for example, to allow the user to make manual adjustments, make selections, enter data or various other information, or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the solution discussed above. The computer readable medium or media can be transportable, such that the program or programs stored thereon can be loaded onto one or more different computers or other processors to implement various aspects of the present solution as discussed above.

The terms "program" or "software" are used herein to refer to any type of computer code or set of computer-executable instructions that can be employed to program a computer or other processor to implement various aspects of embodiments as discussed above. One or more computer programs that when executed perform methods of the present solution need not reside on a single computer or processor, but may be distributed in a modular fashion amongst a number of different computers or processors to implement various aspects of the present solution.

Computer-executable instructions may be in many forms, such as program modules, executed by one or more computers or other devices. Program modules can include routines, programs, objects, components, data structures, or other components that perform particular tasks or implement particular abstract data types. The functionality of the program modules can be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Any references to implementations or elements or acts of the systems and methods herein referred to in the singular can include implementations including a plurality of these elements, and any references in plural to any implementation or element or act herein can include implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementations," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Elements other than 'A' and 'B' can also be included.

The systems and methods described herein may be embodied in other specific forms without departing from the characteristics thereof. The foregoing implementations are illustrative rather than limiting of the described systems and methods.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A system, comprising:
   a first exoskeleton, for at least one of a first foot or a first ankle of a user, comprising:
   an actuator to provide torque about an axis of rotation;
   a sensor; and
   a controller comprising one or more processors, coupled to memory, to:
   communicate, via a wireless connection, one or more packets with a second exoskeleton for the user;
   identify a latency of the wireless connection between the first exoskeleton and the second exoskeleton based on a time difference associated with the one or more packets transmitted between the first exoskeleton and the second exoskeleton during the communication; and
   generate, based on the latency of the wireless connection, a command for the actuator to provide the torque.

2. The system of claim 1, wherein the first exoskeleton comprises a first boot to be worn on the first foot of the user, and the second exoskeleton comprises a second boot to be word by a second foot of the user.

3. The system of claim 1, comprising the first exoskeleton configured to:
   determine a state of the second exoskeleton based on the latency; and
   instruct a component of the first exoskeleton to perform an action based on the state of the second exoskeleton.

4. The system of claim 1, comprising the first exoskeleton configured to:
   output an indication of the latency via a display device; and
   receive, via a user interface, input from the user responsive to the indication.

5. The system of claim 1, comprising the first exoskeleton configured to:
   update a model based on the latency; and
   control, using the updated model, a component of at least one of the first exoskeleton and the second exoskeleton.

6. The system of claim 1, comprising the first exoskeleton configured to:
   modify, based on the latency, a previous command generated prior to identification of the latency of the wireless connection to generate the command; and
   perform, based on the command, an action to cause the actuator of the first exoskeleton to generate torque.

7. The system of claim 1, comprising the first exoskeleton configured to:
   determine a state of the second exoskeleton based on the latency; and
   reject, based on the state of the second exoskeleton, information in a packet received from the second exoskeleton.

8. The system of claim 7, wherein the information of the packet comprises at least one of a gate event, state information, movement information, sensor data, or measurement data.

9. The system of claim 1, comprising the first exoskeleton configured to:
   determine the time difference between transmission of a first packet to the second exoskeleton and receipt of a second packet from the second exoskeleton; and
   determine the latency for communication based on a comparison of the time difference with a threshold.

10. The system of claim 9, comprising:
    the first exoskeleton configured to select a state of the second exoskeleton based on the time difference being greater than the threshold, the state indicating that packets from the second exoskeleton are invalid.

11. An exoskeleton for at least one of a first foot or a first ankle of a user, comprising:
    an actuator to provide torque about an axis of rotation;
    a sensor; and
    a controller comprising one or more processors, coupled to memory, to:
    communicate, via a wireless connection, one or more packets with a second exoskeleton for the user;
    identify a latency of the wireless connection between the exoskeleton and the second exoskeleton based on a time difference associated with the one or more packets transmitted between the exoskeleton and the second exoskeleton during the communication; and
    generate, based on the latency of the wireless connection, a command for the actuator to provide the torque.

12. The exoskeleton of claim 11, comprising a boot to be worn by the user.

13. The exoskeleton of claim 11, wherein the controller is further configured to:
    determine a state of the second exoskeleton based on the latency; and
    instruct a component of the exoskeleton to perform an action based on the state of the second exoskeleton.

14. The exoskeleton of claim 11, wherein the controller is further configured to:

output an indication of the latency via a display device; and receive, via a user interface, input from the user responsive to the indication.

15. The exoskeleton of claim 11, wherein the controller is further configured to:

update a model based on the latency; and control, using the updated model, a component of at least one of the exoskeleton and the second exoskeleton.

16. A method, comprising:

providing a first exoskeleton for at least one of a first foot or a first ankle of a user, the first exoskeleton comprising:

an actuator to provide torque about an axis of rotation;

a sensor; and one or more processors coupled to memory;

communicating, by the one or more processors via a wireless connection, one or more packets with a second exoskeleton for the user;

identifying, by the one or more processors, a latency of the wireless connection between the first exoskeleton and the second exoskeleton based on a time difference associated with the one or more packets transmitted between the first exoskeleton and the second exoskeleton during the communication; and generating, by the one or more processors based on the latency of the wireless connection, a command for the actuator to provide the torque.

17. The method of claim 16, wherein the first exoskeleton comprises a first boot to be worn on the first foot of the user, and the second exoskeleton comprises a second boot to be word by a second foot of the user.

18. The method of claim 16, comprising:

determining, by the one or more processors, a state of the second exoskeleton based on the latency; and instructing, by the one or more processors, a component of the first exoskeleton to perform an action based on the state of the second exoskeleton.

19. The method of claim 16, comprising:

outputting, by the one or more processors, an indication of the latency via a display device; and receiving, by the one or more processors via a user interface, input from the user responsive to the indication.

20. The method of claim 16, comprising:

updating, by the one or more processors, a model based on the latency; and controlling, by the one or more processors using the updated model, a component of at least one of the first exoskeleton and the second exoskeleton.

* * * * *